United States Patent
Barrow et al.

(10) Patent No.: US 6,515,023 B2
(45) Date of Patent: Feb. 4, 2003

(54) THROMBIN RECEPTOR ANTAGONISTS

(75) Inventors: James C. Barrow, Harleysville, PA (US); Philippe G. Nantermet, Lansdale, PA (US); Harold G. Selnick, Ambler, PA (US); John H. Hutchinson, Philadelphia, PA (US); Michael J. Breslin, Drexel Hill, PA (US); Kristen L. Glass, Elkins Park, PA (US); Thomas M. Connolly, Lansdale, PA (US); Andrew Stern, Lower Gwynedd, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/772,353

(22) Filed: Jan. 30, 2001

(65) Prior Publication Data

US 2002/0007045 A1 Jan. 17, 2002

Related U.S. Application Data

(60) Provisional application No. 60/179,184, filed on Jan. 31, 2000.

(51) Int. Cl.[7] ........................ A61K 31/44; A61K 31/40; A61K 31/38; A61K 31/23; A61K 31/17
(52) U.S. Cl. ................ 514/597; 514/303; 514/350; 514/423; 514/438; 514/552; 546/118; 546/318; 546/323; 548/537; 549/77; 558/417; 560/27; 564/49; 564/51
(58) Field of Search .................. 564/51, 49; 514/597, 514/303, 350, 423, 438, 552; 541/118, 318, 323; 548/537; 549/77; 558/417; 560/27

(56) References Cited

U.S. PATENT DOCUMENTS

| 5,446,131 A | 8/1995 | Maraganore |
| 5,457,177 A | 10/1995 | Veber et al. |
| 5,516,889 A | 5/1996 | Hollenberg et al. |
| 5,773,459 A | * 6/1998 | Tang et al. .................. 514/445 |
| 5,866,681 A | 2/1999 | Scarborough |
| 6,017,890 A | 1/2000 | Hoekstra et al. |
| 6,063,847 A | 5/2000 | Chackalamannil et al. |
| 6,093,742 A | * 7/2000 | Salituro et al. ............. 514/596 |
| 6,156,732 A | 12/2000 | Hoekstra et al. |

FOREIGN PATENT DOCUMENTS

WO    WO 94/03479    2/1997

OTHER PUBLICATIONS

Tiers, Chem. Abst. 110:66645 (1989).*
Bernatowicz, Michael, S. et al., "Development of Potent Thrombin Receptor Antagonict Peptides", *J. Med. Chem.*, pp. 4879–4887; 39: 1996.
Alexopoulos, K. et al., "A comparative SAR study of thrombin receptor derived non peptied mimetics: Importance of phenyl/guanidino proximity for activity", *Amino Acids*, pp. 211–220; 15: 1998.

* cited by examiner

*Primary Examiner*—Peter O'Sullivan
(74) *Attorney, Agent, or Firm*—Richard S. Parr; Melvin Winokur; Valerie J. Camara

(57) ABSTRACT

A thrombin receptor antagonist having the formula

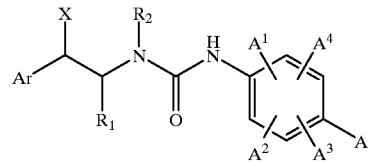

useful for inhibiting the aggregation of blood platelets. The compounds can be used in a method of acting upon a thrombin receptor which comprises administering a therapeutically effective but non-toxic amount of such compound to a mammal, preferably a human.

8 Claims, No Drawings

THROMBIN RECEPTOR ANTAGONISTS

This application claims the benfit of provisional application 60/179,184 filed Jan. 31, 2000.

BACKGROUND OF THE INVENTION

Thrombin is able to elicit many cellular responses (e.g. thrombotic, inflammatory, proliferative and atherosclerotic) that are mediated by proteolytic activation of a specific cell surface receptor known as the thrombin receptor (Vu et al. (1991) *Cell* 64: 1057–1068; Rasmussen et al. (1991) *FEBS Lett* 288: 123–128; Zhong et al. (1992) *J. Biol. Chem.* 267: 16975–16979; Bahou et al. (1993) *J. Clin. Invest.* 91: 1405–1413; McNamara et al. (1993) *J. Clin. Invest.* 91: 94–98; Glembotski (1993) *J. Biol. Chem.* 268: 20646–20652; and Park et al. (1994) *Cardiovasc. Res.* 28: 1263–1268. The thrombin receptor has seven transmembrane-spanning domains and belongs to a family of G-protein coupled receptors (Vu et al. (1991) *Cell* 64: 1057–1068 and Schwartz (1994) *Current Opin. Biotechnol.* 5: 434–444). The thrombin receptor is a specific tethered ligand receptor or protease activated receptor. Activation of the receptor occurs by thrombin cleavage of an extracellular N-terminal domain. The new N-terminus through intramolecular interaction activates the receptor (Vu et al. (1991) *Cell* 64: 1057–1068; Coughlin (1993) *Thromb. Haemostas.* 70: 184–187; Van Obberghen-Schilling and Pouyssegur (1993) *Thromb. Haemostas.* 70: 163–167; Brass et al. (1994) *Ann. NY Acad. Sci.* 714: 1–12). Synthetic thrombin receptor activating peptides comprising the 6–14 amino acids of the tethered ligand were found to activate platelets equally with thrombin itself and are considered to be full agonists (Vu et al. (1991) *Cell* 64: 1057–1068; Vassallo et al. (1992) *J. Biol. Chem.* 267: 6081–6085; Coller et al. (1992) *Biochemistry* 31: 11713–11722; Chao et al. (1992) *Biochemistry* 31 6175–6178; Rasmussen et al. (1993) *J. Biol. Chem.* 268: 14322–14328). The first five amino acids (SFLLR) are required for activation of the platelet thrombin receptor (Scarborough et al. (1992) *J. Biol. Chem.* 267: 13146–13149;Hui et al. (1992) *Biochem. Biophys. Res. Commun.* 184: 790–796). Structure activity studies, NMR experiments and molecular modeling have determined the specific requirements for each amino acid in SFLLR (Matsoukas et al. (1997) *J. Prot. Chem.* 16: 113–131; Natarajan et al. (1995) *Int. J. Pept. Protein Res.* 45: 145–151).

Antagonists of the thrombin receptor are medicinally useful agents for blocking the unwanted effects of thrombin on cells.

SUMMARY OF THE INVENTION

Compounds of the invention are useful for inhibiting the aggregation of blood platelets. The above-mentioned compounds, which are thrombin receptor antagonists, can be used in a method of acting upon a thrombin receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of active drug is another feature of this invention.

DETAILED DESCRIPTION OF THE INVENTION

The present invention includes compounds having the structure

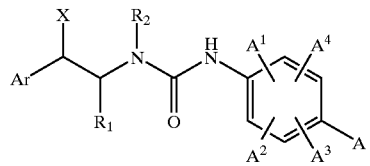

and pharmaceutically acceptable salts thereof, wherein
$R^1$ is hydrogen or $C_{1-10}$ alkyl;
$R^2$ is
  $C_{1-10}$ alkyl,
  $C_{3-8}$ cycloalkyl,
  $CH(CH_3)CH_2OCH_3$,
  $CH(CH_3)CH_2F$,
  $CH(CH_3)CH_2SCH_3$,
A is hydrogen or

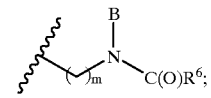

$A^1$, $A^2$, $A^3$, and $A^4$ are independently selected from
  hydrogen,
  halogen,
  nitro,
  CN,
  $R^{10}$,
  $OR^{10}$,
  $NR^{10}R^{11}$;
m is 0, 1, 2, 3, 4, or 5;
B is
  hydrogen,
  $R^{12}$,
  $C_{3-8}$ cycloalkyl,
  $CH(CH_3)CH_2OCH_3$,
  $CH(CH_3)CH_2F$,
  $CH(CH_3)CH_2SCH_3$;
$R^6$ is
  $R^{13}$,
  $Ar^2$,
  $NH(Ar^2)$,
  $C_{3-8}$ cycloalkyl,
  $CH_2Ph$,
  $C(CH_3)_2NC(O)OC(CH_3)_3$,
  $C(NH_2)(CH_3)_2$, or
  $OC(CH_3)_3$,
X is
  OH,
  $OR^4$,
  $OC(O)R^4$,
  $OC(O)Ar^1$,
  $NR^4Ar^1$,
  $SR^4$,

S(O)R⁴,
SO₂R⁴;

R⁴, R⁹, R¹⁰, R¹¹, R¹², and R¹³ are independently selected from hydrogen or $C_{1-10}$ alkyl; and Ar, Ar¹ and Ar² are independently selected from the group consisting of i) aryl, unsubstituted, monosubstituted, independently disubstituted or independently trisubstituted with
 $C_{1-10}$ alkyl,
 CH₂NHC(O)NH₂,
 halogen,
 CN,
 amino $C_{1-10}$ alkyl,
 CF₃, or
 S(O)$_n$R³, wherein R³ is hydrogen or $C_{1-10}$ alkyl, or ii) heteroaryl, unsubstituted, monosubstituted, independently disubstituted or independently trisubstituted with
 $C_{1-10}$ alkyl,
 halogen,
 CN,
 amino $C_{1-10}$ alkyl,
 CF₃, or
 S(O)$_n$R³, wherein R³ is hydrogen or $C_{1-10}$ alkyl.

In a class of compounds of the invention, and pharmaceutically acceptable salts thereof, R⁴ is CH₃, C(CH₃)₃, or CH₂CH₃;
R¹⁰ is CH₃;
R¹³ is CH(CH₃)₂, CH₂CH₃, or CH₃;
Ar² is phenyl, unsubstituted, monosubstituted or independently disubstituted with F, S(O)₂NH₂, Cl, CH₂NHC(O)NH₂, or CH₃,

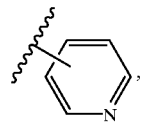

unsubstituted, monosubstituted or independently disubstituted with F,

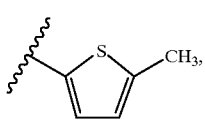

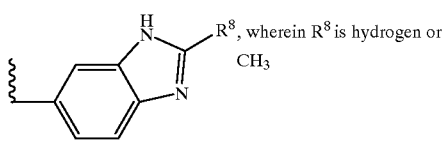, wherein R⁸ is hydrogen or CH₃

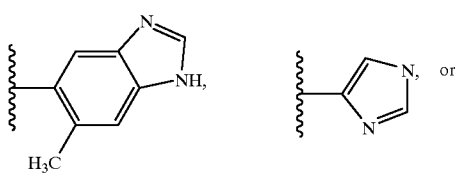

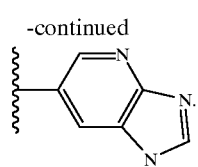

In a group of the class of compounds, and pharmaceutically acceptable salts thereof,
Ar is

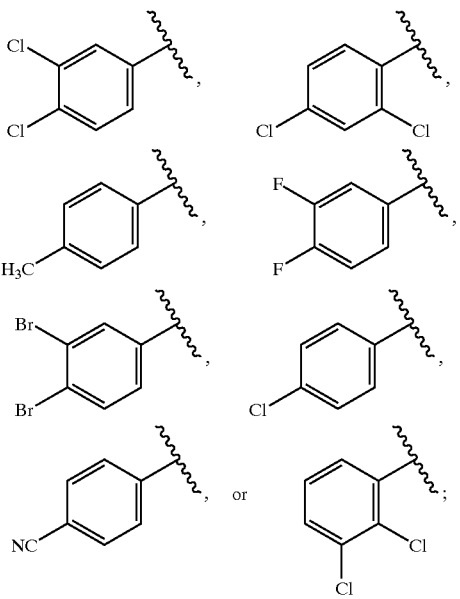

X is
 OH,
 OCH₃,
 OC(O)C(CH₃)₃,
 OC(O)C₃,

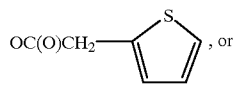, or

OCH₂CH₃;
R² is
 CH(CH₃)₂,
 C(CH₃)₃,
 CH₂CH₃,

, ,

CH₂CH₂CH₃,
 CH(CH₃)₂CH₂CH₃,
 CH(CH₃)CH₂CH₃,
 CH(CH₂CH₃)₂,
 CH(CH₃)CH₂OCH₃,
 CH(CH₃)CH₂CH₂CH₃,
 CH(CH₃)CH₂F, or
 CH(CH₃)CH₂SCH₃;

$A^1$ is
  hydrogen,
  Cl,
  F,
  $CH_3$, or
  CN;
$A^2$ is
  hydrogen,
  F, or
  $OCH_3$;
$A^3$ and $A^4$ are hydrogen;
m is 0, 1, or 2;
B is hydrogen;
$R^6$ is
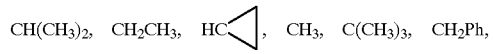
$CH(CH_3)_2$, $CH_2CH_3$, HC△, $CH_3$, $C(CH_3)_3$, $CH_2Ph$,
$CH_3$,
$C(CH_3)_3$,
$CH_2Ph$,
Ph,
$C(CH_3)_2NC(O)OC(CH_3)_3$,
$C(NH_2)(CH_3)_2$,
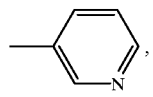 , 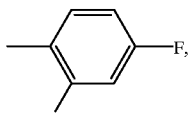 ,
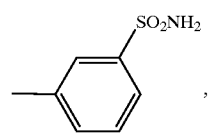 , 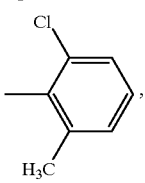 ,
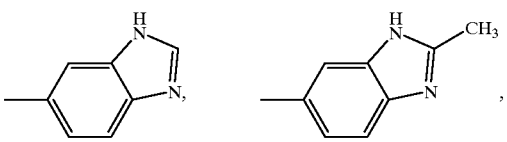
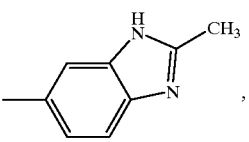
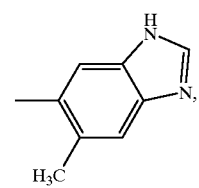 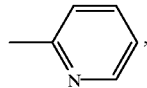
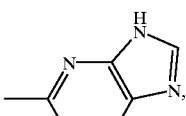 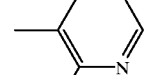 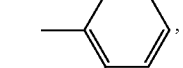
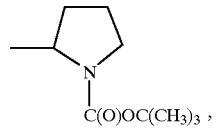 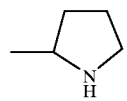 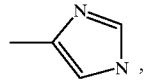
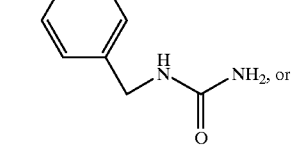 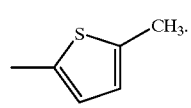
Examples of the group of compounds include
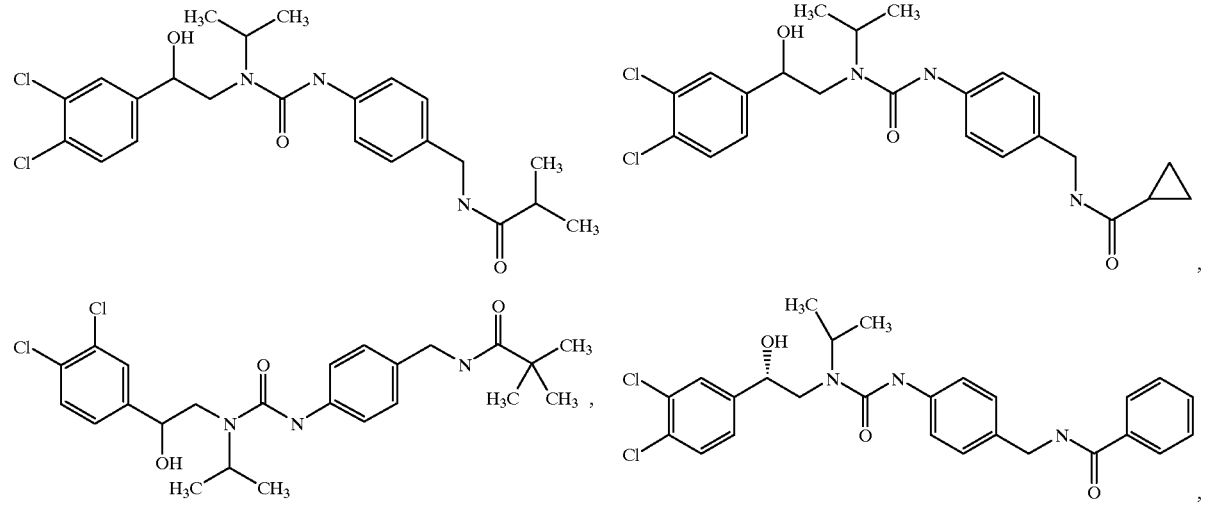

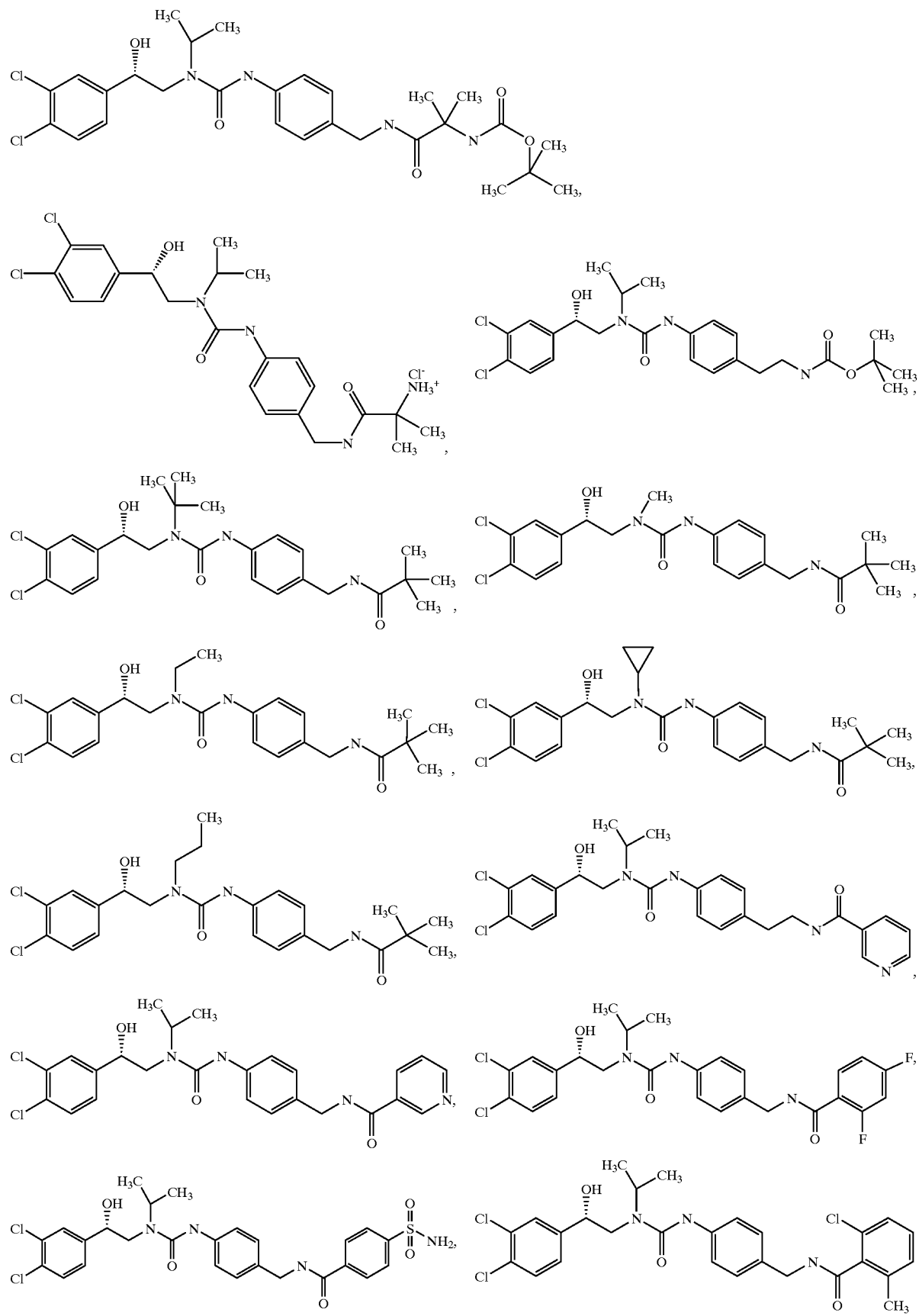

-continued
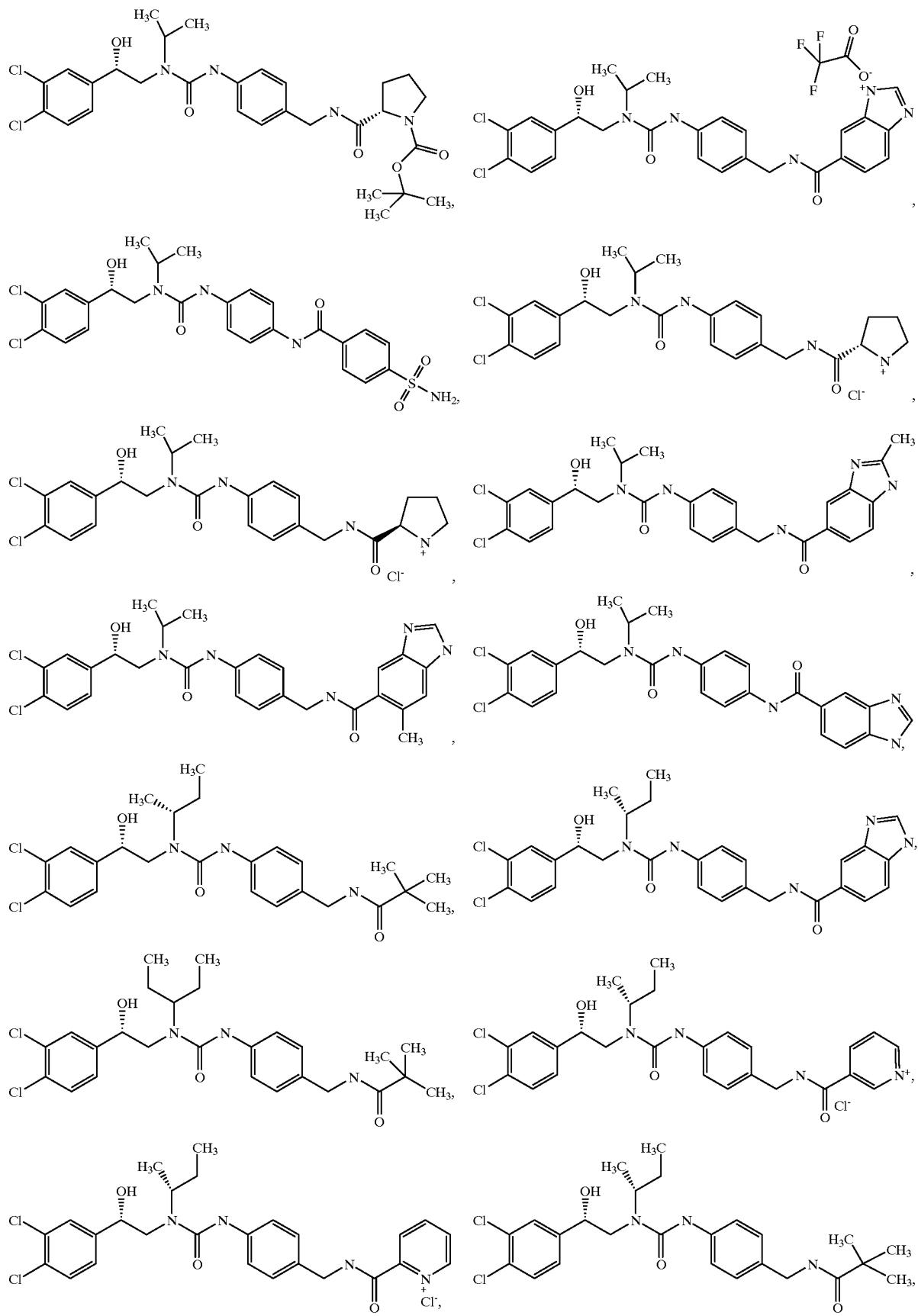

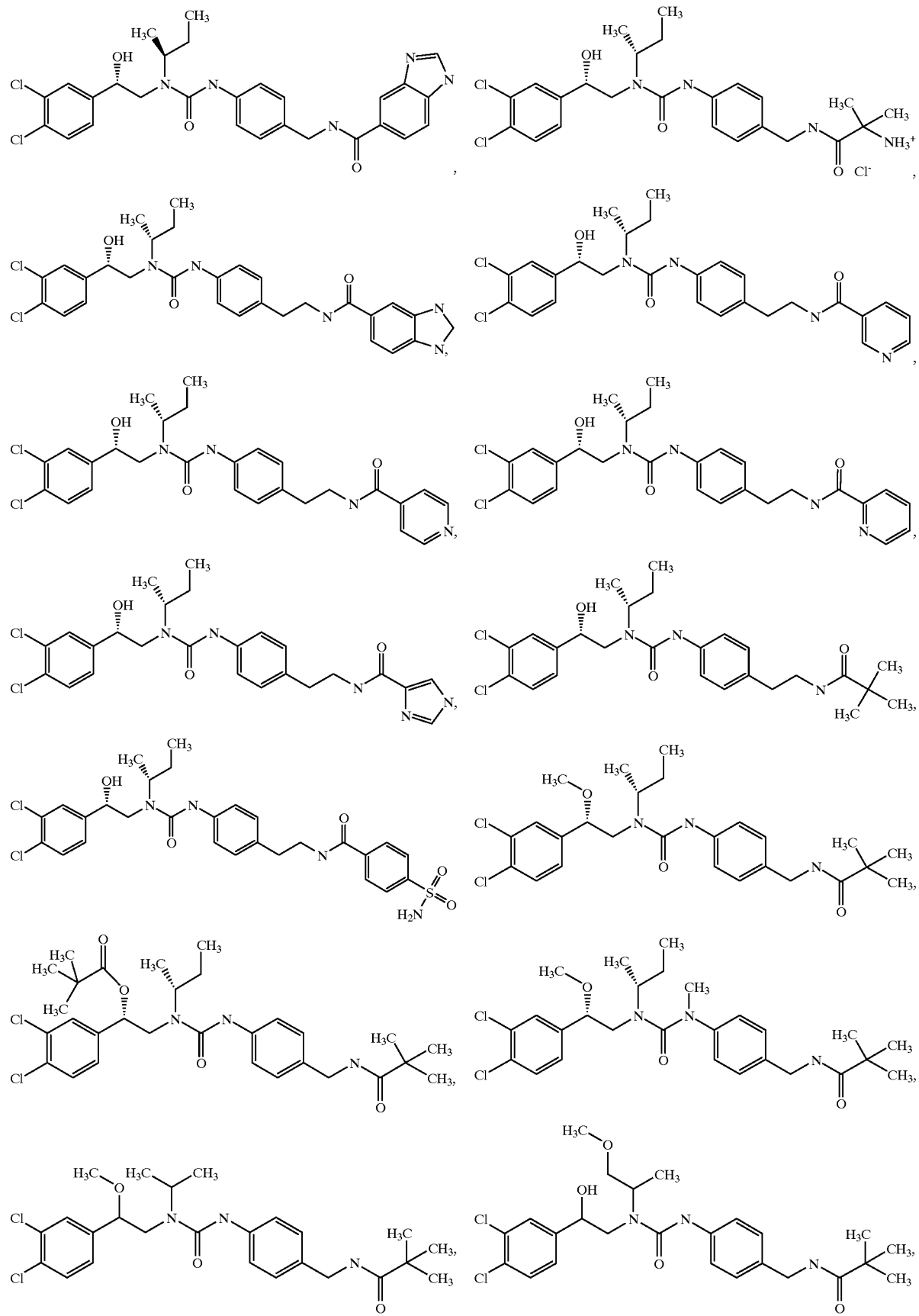

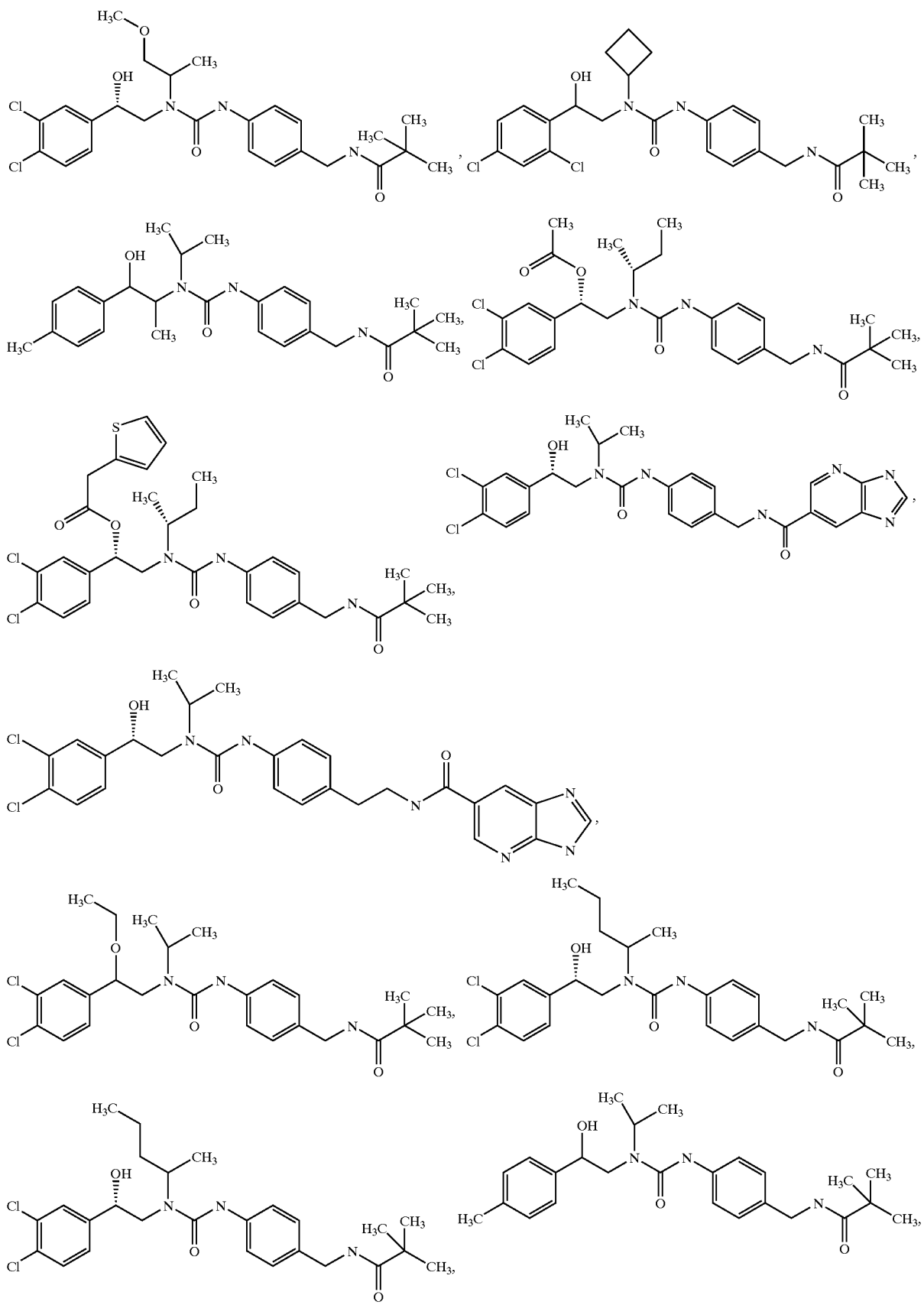

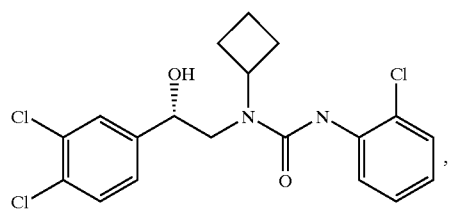
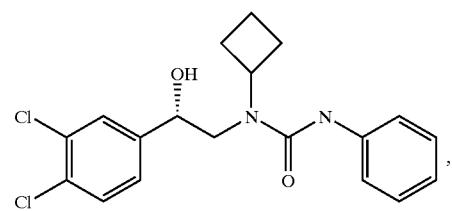
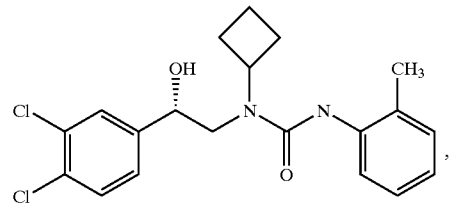
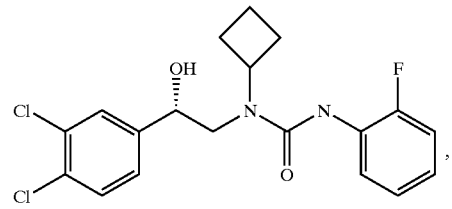
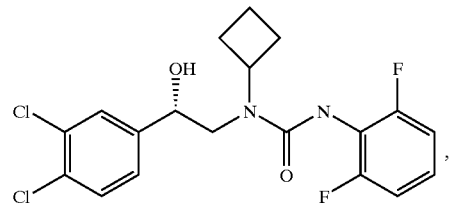
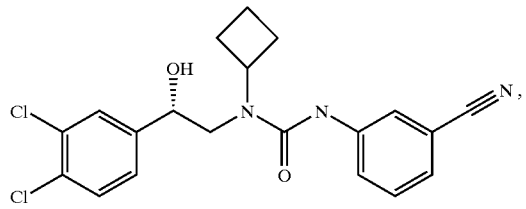
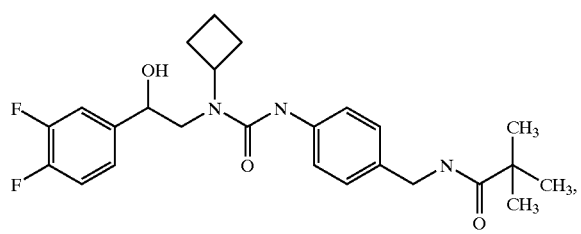
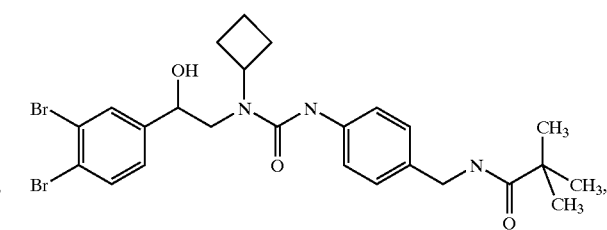
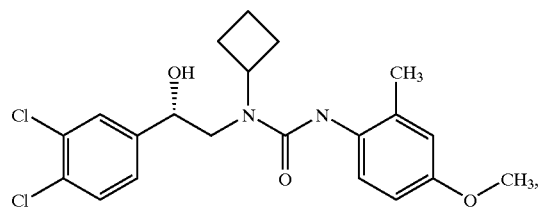
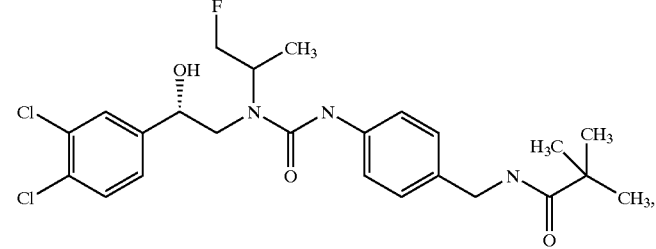
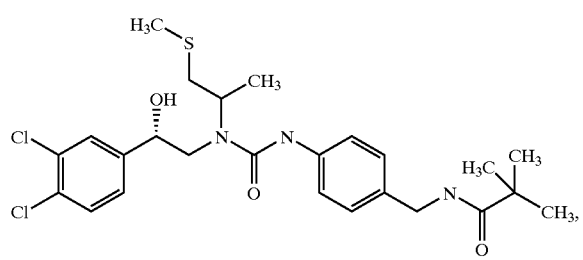
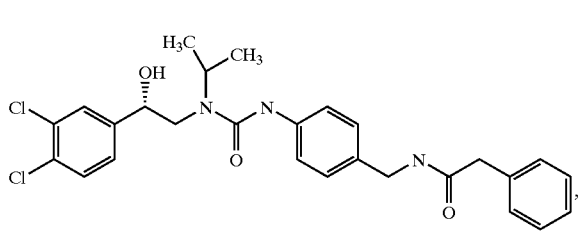
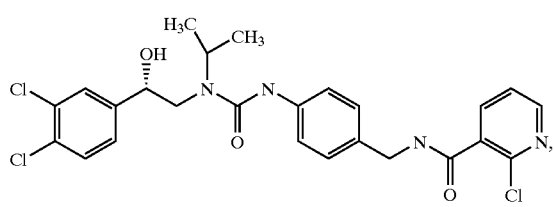
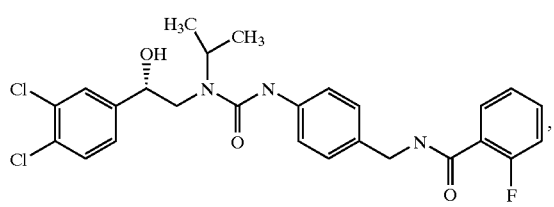

-continued
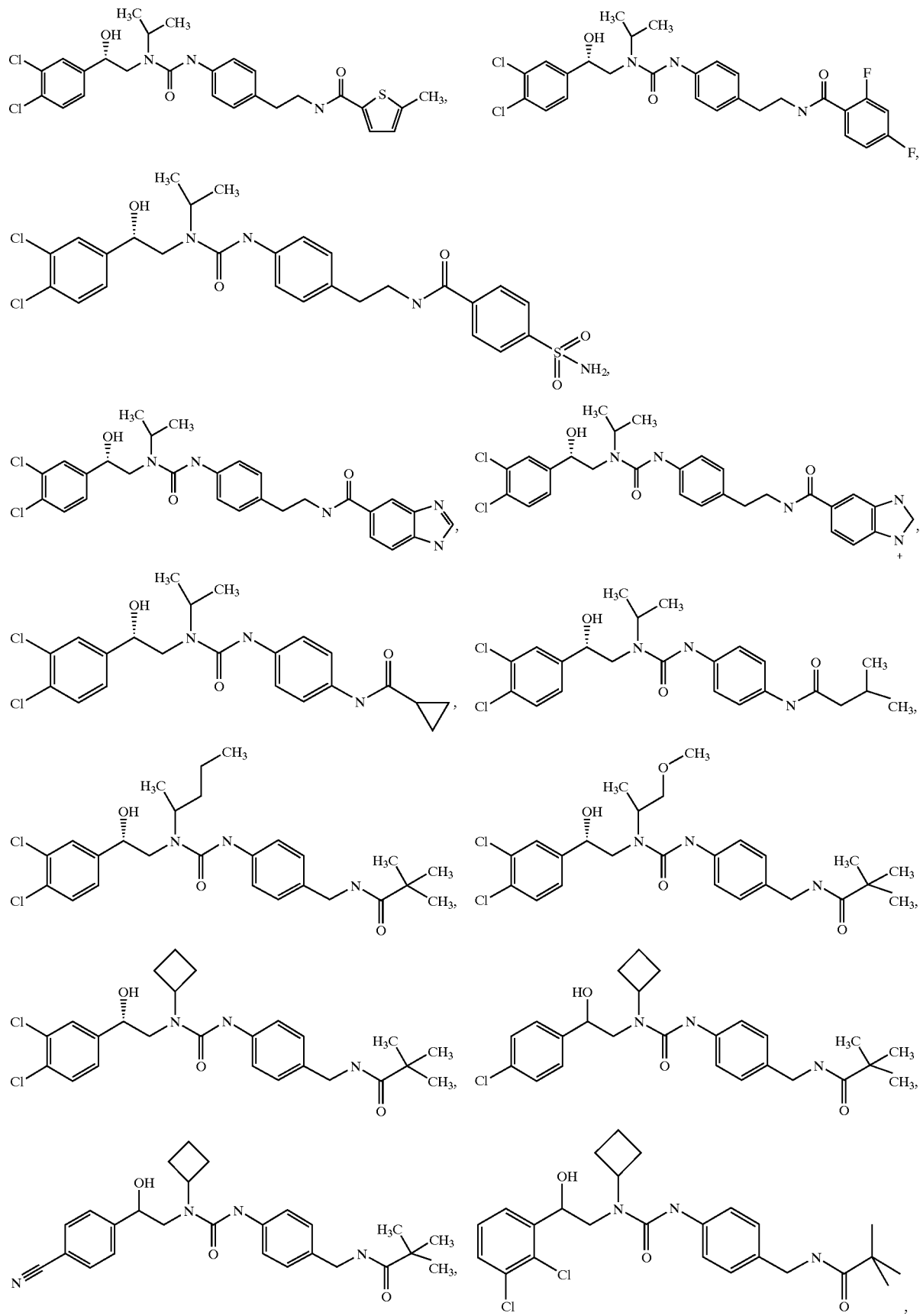

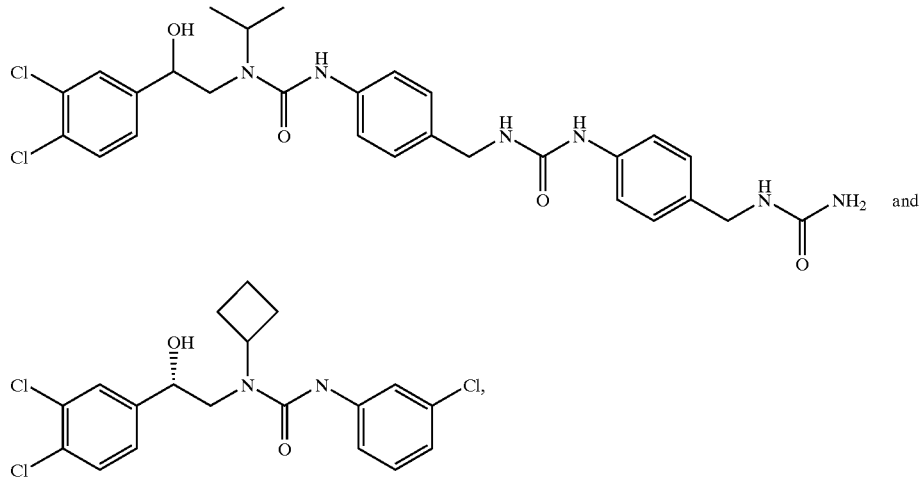

and pharmaceutically acceptable salts thereof.

The term "alkyl" means branched or straight-chain saturated aliphatic hydrocarbon groups having the specified number of carbon atoms (for example, "$C_{1-10}$" denotes alkyl having 1 to 10 carbon atoms, e.g., methyl, ethyl, n-propyl, isopropyl, n-butyl, isobutyl, sec-butyl, tert-butyl, pentyl, iso-amyl, hexy, octyl radicals and the like.

The term "alkenyl" means hydrocarbon chains of either a straight of branched configuration and one or more unsaturated carbon—carbon bonds which may occur at an stable point along the chain, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like.

The term, "alkynyl" means hydrocarbon chains of either a straight or branched configuration and one or more triple carbon—carbon bonds which may occur in any stable point along the chain, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alkoxy" means an alkyl group of indicated number of carbon atoms attached through an oxygen bridge, e.g., methoxy, ethoxy, n-propoxy, isopropoxy, n-butoxy, isobutoxy, sec-butoxy, tert-butoxy, pentyloxy, radicals and the like.

The terms "alkylene", "alkenylene", "phenylene", and the like, refer to alkyl, alkenyl, and phenyl groups, respectively, which are connected by two bonds to the rest of the structure. Such "alkylene", "alkenylene", "phenylene", and the like, may alternatively and equivalently be denoted herein as "-(alkyl)-", "-(alkenyl)-" and "-(phenyl)-", and the like.

The term "halogen" includes fluorine, chlorine, iodine and bromine.

The term "oxy" means an oxygen (O) atom.

The term "thio" means a sulfur (S) atom.

The term "aryl" means a partially saturated or fully saturated 6–14 membered ring system such as for example, phenyl, naphthyl or anthracyl. The term "Ph", which appears in certain chemical formulas in the specification and claims, represents phenyl.

The term "cycloalkyl" means saturated ring groups, including mono-, bi-, or poly-cyclic ring systems such as cyclopropyl, cyclobutyl, cyclopentyl, cyclohexy, cycloheptyl, cyclooctyl, adamantyl, and the like.

The term "heterocyclic" or "heterocycle" means a stable 5- to 7-membered monocyclic or bicyclic or 7- to 10-membered bicyclic heterocyclic ring which may be saturated, partially unsaturated, or fully unsaturated, which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of heterocyclic rings include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxanthiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

The term "heteroaryl" means an unsaturated heterocyclic group, preferably 5 or 6-membered monocyclic ring systems or 8–10 membered fused bicyclic groups, having heteroatoms selected from the group consisting of N, O, and S, for example, pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

Under standard nonmenclature used throughout this disclosure, the terminal portion of the designated side chain is described first followed by the adjacent functionality toward the point of attachment. For example, a methylene substituted with ethylcarbonylamino is equivalent to

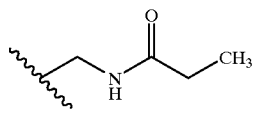

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention. Thus, the term "active drug" includes a compound of the invention and its salts, racemic mixtures or separated enantiomers, hydrates or anhydrous forms, polymorphs, and pharmaceutically acceptable salts.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Prodrugs, such as ester derivatives of active drug are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

In the schemes and examples below, various reagent symbols have the following meanings:

| | |
|---|---|
| BOC (or Boc): | t-butyloxycarbonyl |
| Pd—C: | Palladium on activated carbon catalyst |
| DMF: | Dimethylformamide |
| DMSO: | Dimethylsulfoxide |
| CBZ: | Carbobenzyloxy |
| $CH_2Cl_2$: | Methylene chloride |
| $CHCl_3$: | chloroform |

-continued

| | |
|---|---|
| EtOH: | ethanol |
| MeOH: | methanol |
| EtOAc: | ethyl acetate |
| HOAc: | acetic acid |
| BOP: | Benzotriazol-1-yloxytris(dimethylamino)phosphonium, hexafluorophosphate |
| EDC: | 1-(3-Dimethylaminopropyl)-3-ethylcarbodiimide hydrochloride |
| Oxone: | potassium peroxymonosulfate |
| LDA: | Lithium diisopropylamide |

Active drug can be administered in such oral forms as tablets, capsules (each of which includes sustained release or timed release formulations), pills, powders, granules, elixirs, tinctures, suspensions, syrups, and emulsions. Likewise, it may be administered in intravenous (bolus or infusion), intraperitoneal, subcutaneous, or intramusculsar form, all using forms well known to those of ordinary skill in the pharmaceutical arts. An effective but non-toxic amount of active drug can be employed as an anti-aggregation agent.

Active drug may be administered to patients where prevention of thrombosis by inhibiting binding of thrombin to the thrombin receptor is desired. It is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Active drug may be administered to these surgical patients to prevent the formation of thrombi and thromboemboli.

Other applications of active drug include prevention of platelet thrombosis, thromboembolism and reocclusion during and after thrombolytic therapy and prevention of platelet thrombosis, thromboembolism and reocclusion after angioplasty or coronary artery bypass procedures. It may also be used to prevent myocardial infarction.

The dosage regimen utilizing active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mg/kg/day. For example, a typical 90 kg patient would receive oral dosages ranging between about 0.45 mg/day and about 4.5 g/day, most preferably between about 1.0 mg/day and 1.0 g/day. Suitable pharmaceutical oral compositions such as tablets or capsules may contain 1–500 mg, for example, 1 mg, 10 mg, 100 mg, 200 mg and 500 mg. Intravenously, the most preferred doses will range from about 0.5 to about 5 mg/kg/minute during a constant rate infusion. Active drug may be administered in one or divided doses of two, three, or four times daily. Furthermore, active drug can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the active drug can form the active ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl- methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolyric agents less than the usual doses of those agents.

Compounds of the invention were prepared according to the following general schemes, including the specific procedures described in the following examples. Those skilled in the art will readily understand that known variations of the conditions and processes of the following preparative procedures can be used to prepare these compounds. All temperatures are degrees Celsius unless otherwise noted.

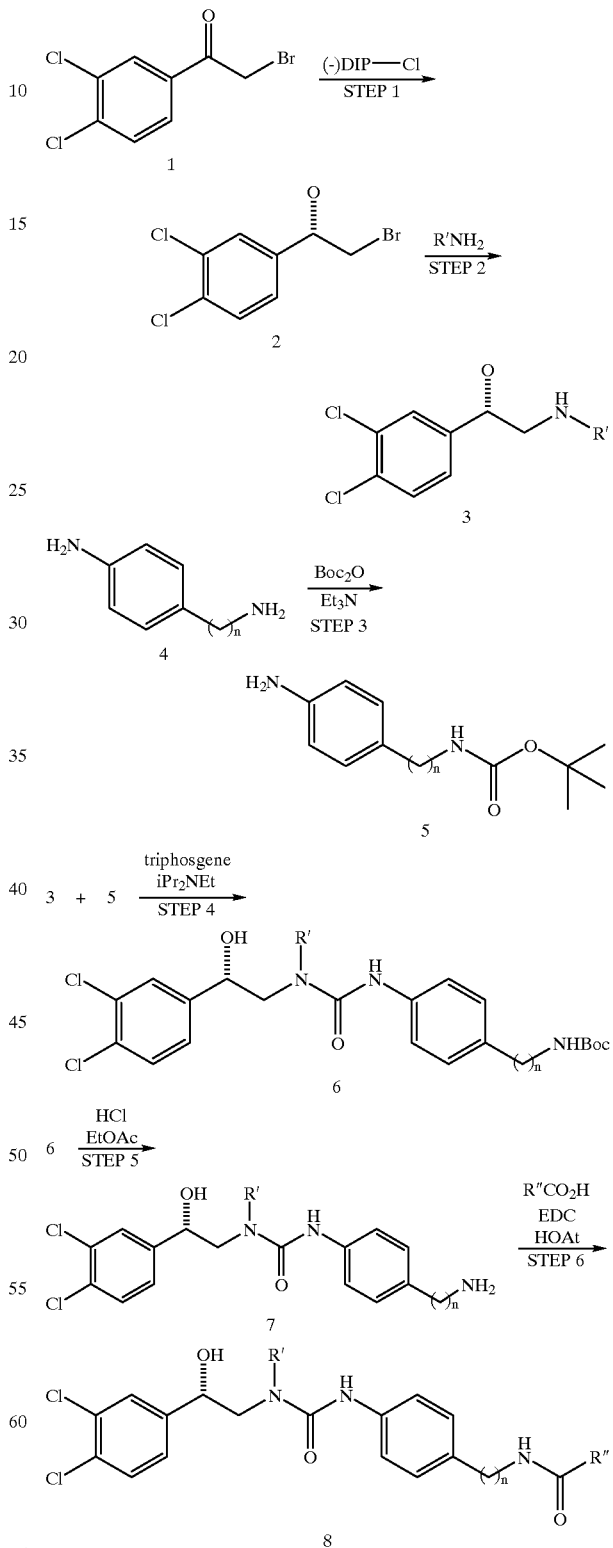

For example, in the above scheme, R' can be isopropyl or the like, n can be 1, and R" can be 5 (1H-benzimidazole) or the like.

Scheme 2

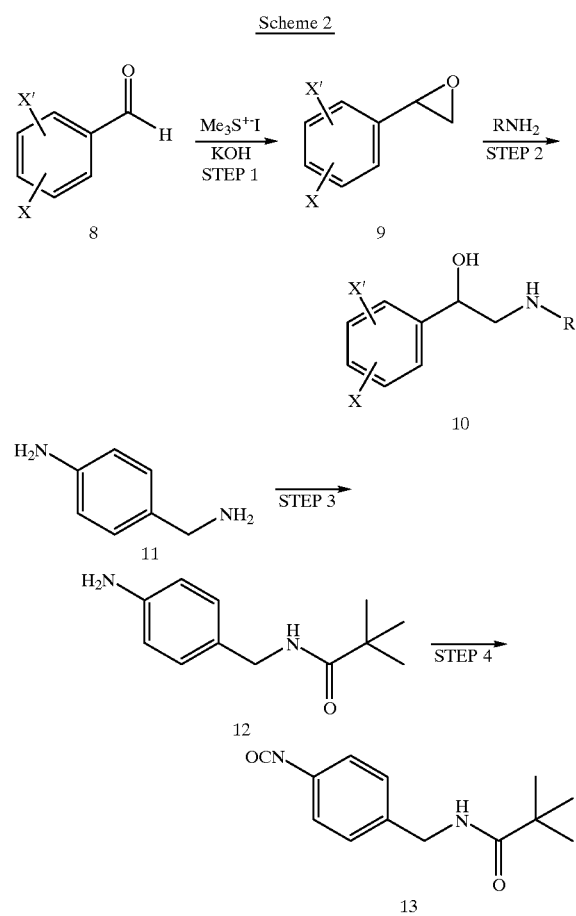

For example, in the above scheme, X and X' can independently be hydrogen or halogen.

Scheme 3

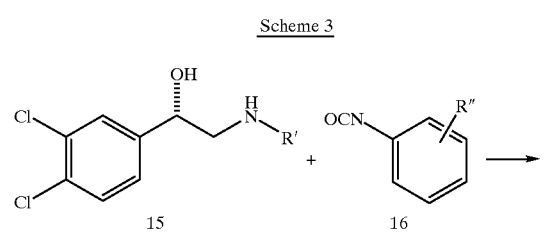

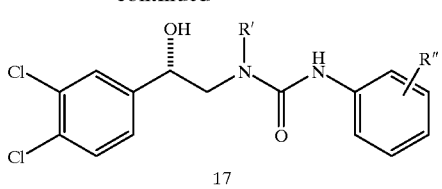

For example, in the above scheme, R' can be cyclobutyl or the like and R" can be chloro, e.g. meta chloro, or the like.

Scheme 4

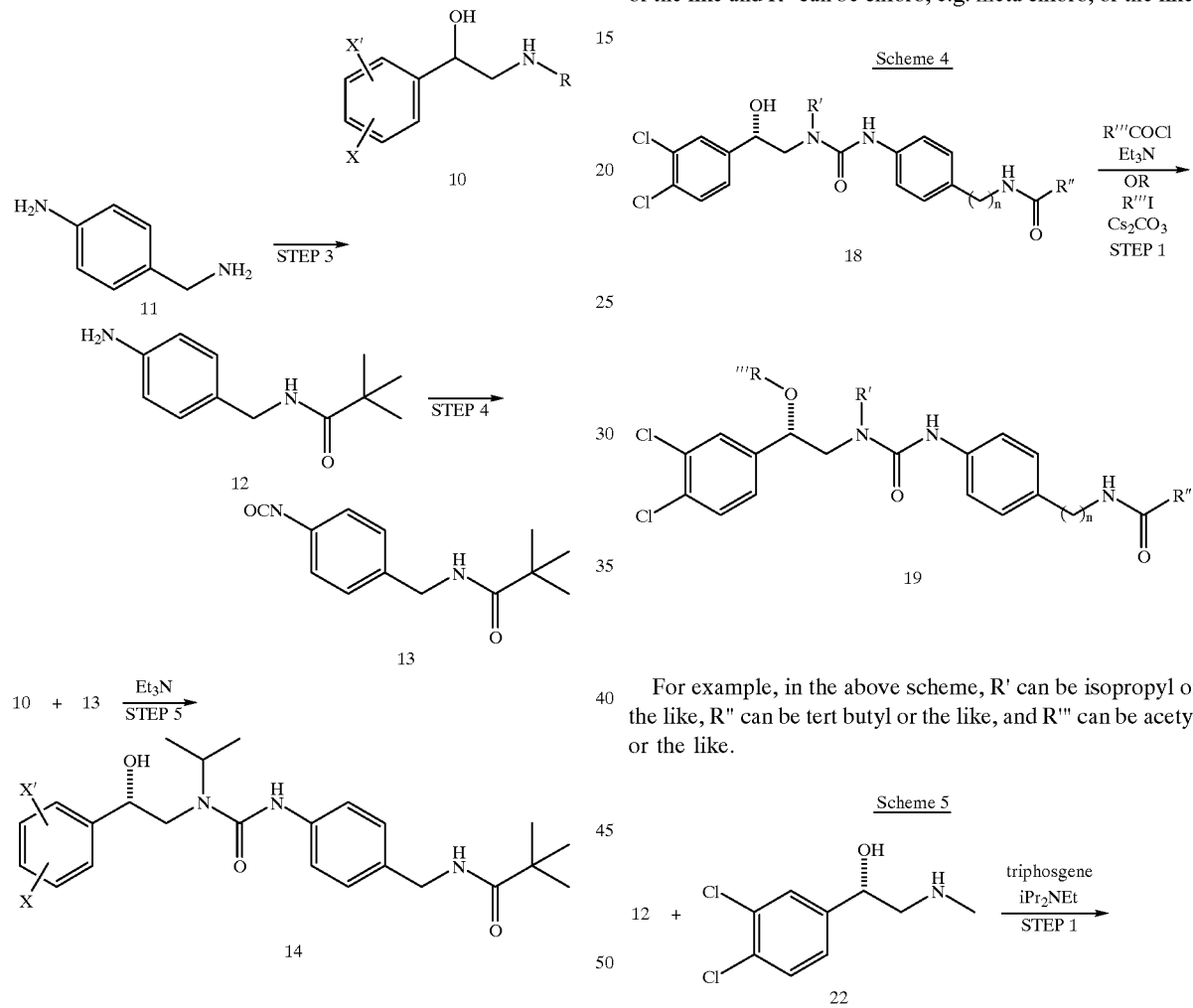

For example, in the above scheme, R' can be isopropyl or the like, R" can be tert butyl or the like, and R'" can be acetyl or the like.

Scheme 5

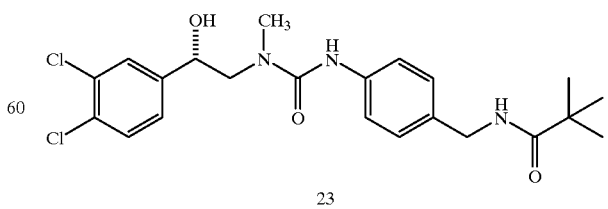

Scheme 6

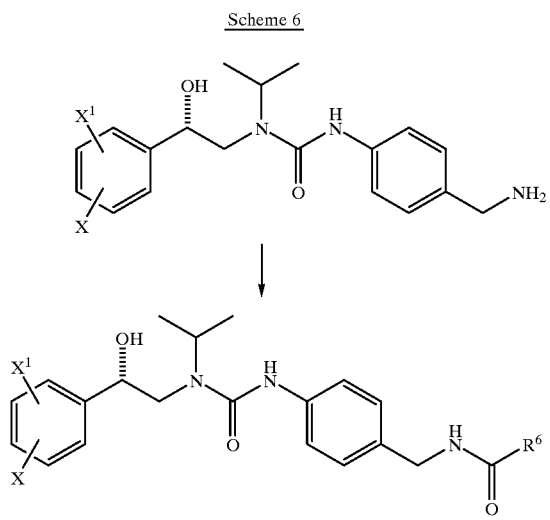

For example, in the above scheme, X and X' can independently be hydrogen or halogen, and $R^6$ is $NH(Ar^2)$.

Compounds of the invention may also be prepared according to general procedures outlined in S. Hutchins et al. *Tetrahedron Lett.*, 1995, 36, 2583–2586 and S. Hutchins et al. *Tetrahedron Lett.*, 1994, 35, 4055–4058.

EXAMPLE 1

This example illustrates Scheme 1.

Step 1

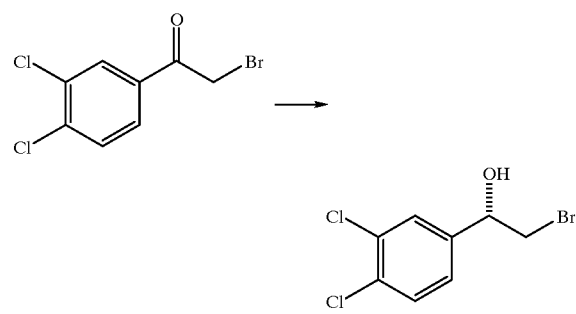

2-bromo-1-(3,4-dichlorophenyl)ethanol

To a 0° C. solution of 13 g (49 mmol) 2-bromo-1-(3,4-dichlorophenyl)ethanone in 250 ml THF was added 17 g (53 mmol) (+)-B-chlorodiisopinocampheyl-borane. The reaction mixture was stirred 6 hours at 0° C., then allowed to warm to room temperature and stir 14 hours. An additional 2 g (6 mmol) of (+)-B-chlorodiisopinocampheyl-borane was added and the reaction mixture stirred 4 more hours, then concentrated in vacuo. To this was added 250 ml ether and 10 ml diethanolamine and the resulting slurry stirred for 2 hours, then filtered through celite. The filtercake was washed 2×200 ml ether and the combined filtrates washed with 500 ml 10% aqueous $KHSO_4$, 500 mL saturated aqueous $NaHCO_3$, and 500 mL brine, then dried over $MgSO_4$, filtered and concentrated. Purification by flash chromatography (9×20 cm silica gel, 100% $CH_2Cl_2$) afforded 11.2 g 2-bromo-1-(3,4-dichlorophenyl)ethanol. $^1H$ NMR(300 mHz, $CDCl_3$) 7.52 (d, 1H, J=3 Hz); 7.45 (d, 1H, J=9 Hz); 7.22 (dd, 1H, J=9and 3 Hz); 4.70 (dt, 1H, J=9 and 3.4 Hz); 3.62 (dd, 1H, J=11 and 3.4 Hz); 3.49 (dd, 1H; J=11 and 9 Hz); 2.66 (d, 1H; J=3.4 Hz)

Step 2

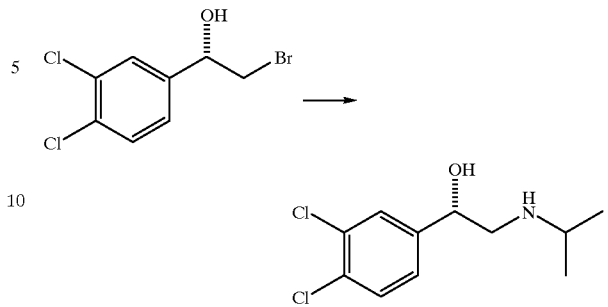

2-isopropylamino-1-(3,4-dichlorophenyl)ethanol

A mixture of 3.9 g (14 mmol) 2-bromo-1-(3,4-dichlorophenyl)ethanol and 10 ml isopropylamine was sealed and heated to 80° C. for 16 h, then cooled to room temperature, diluted with 500 mL EtOAc, washed with 400 mL saturated aqueous $NaHCO_3$, and 500 mL brine, then dried over $Na_2SO_4$, filtered and concentrated. Purification by flash chromatography (5×8 cm silica gel, elute with 250 mL 3%MeOH/$CH_2Cl_2$, 100 mL 50% EtOH/$CH_2Cl_2$, then 200 mL EtOH) afforded 2.7 g 2-isopropylamino-1-(3,4-dichlorophenyl)ethanol. $^1H$ NMR(400 mHz, $CDCl_3$) 7.48 (d, 1H, J=1.92 Hz); 7.40 (d, 1H, J=8.22 Hz); 7.20 (dd, 1H, J=8.23and 1.92 Hz); 4.59 (dd, 1H, J=8.96 and 3.75 Hz); 2.94 (dd, 1H, J=12.2 and 3.66 Hz); 2.83 (sept, 1H, J=6.31 Hz); 2.57 (dd, 1H, J=12.3 and 8.87 Hz); 1.09 (d, 3H, J=6.31 Hz); 1.08 (d, 3H, J=6.22 Hz).

Step 3

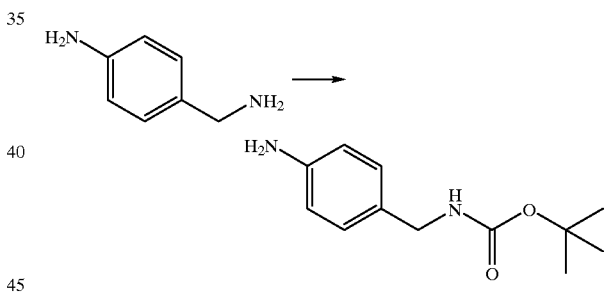

4-aminobenzylamine, tertbutylcarbamate

To a 0° C. solution of 5 ml (44 mmol) 4-aminobenzylamine in 400 mL $CH_2Cl_2$ was added 6.8 mL (48 mmol) triethylamine and 9.5 g (44 mmol) di-tert-butyldicarbonate. The reaction mixture was allowed to warm to room temperature and stir 14 hours. The reaction mixture was then diluted with 800 mL EtOAc, washed with 700 mL each of water, saturated aqueous $NaHCO_3$, and brine, then dried over $Na_2SO_4$, filtered and concentrated to provide 9.5 g. 4-aminobenzylamine, tertbutylcarbamate. $^1H$ NMR(300 mHz, $CDCl_3$) 7.07 (d, 2H, J=8.6 Hz); 6.62 (d, 2H, J=8.6 Hz); 4.75 (s, 1H); 4.20 (d, 1H, J=5 Hz); 3.62 (br s, 2H); 1.44 (s, 9H)

Step 4

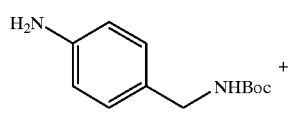

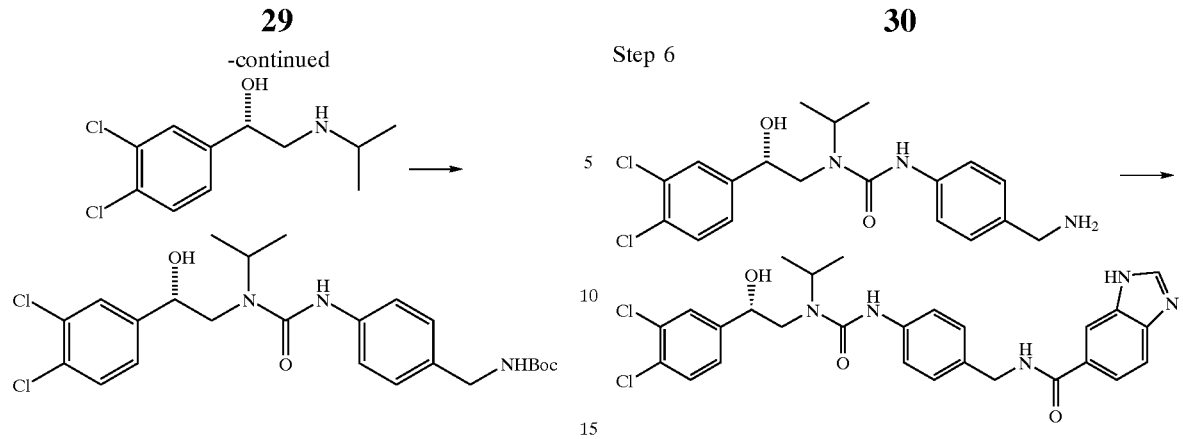

(4-{3-[2-(3,4-Dichloro-phenyl)-2-hydroxy-ethyl]-3-isopropyl-ureido}-benzyl)-carbamic acid tert-butyl ester To a solution of 0.89 g (3 mmol) triphosgene in 10 ml CH$_2$Cl$_2$ was added a solution of 2.0 g (8 mmol) 4-aminobenzylamine, tertbutylcarbamate and 1.69 ml (9.7 mmol) diisopropylethylamine in 25 ml CH$_2$Cl$_2$ dropwise over 1 hour. After the addition was complete, a solution of 1.79 g (8 mmol) 2-isopropylamino-1-(3,4-dichlorophenyl)-ethanol and 1.69 ml (9.7 mmol) diisopropylethylamine in 25 ml CH$_2$Cl$_2$ was added over 5 min. The reaction mixture was stirred for 10 min. diluted with 200 ml EtOAc, washed with 200 ml each of saturated aqueous NaHCO$_3$, water, and brine, then dried over Na$_2$SO$_4$, filtered and concentrated. Purification by flash chromatography (50% EtOAc/hexanes) provided 4 g (4-{3-[2-(3,4-Dichloro-phenyl)-2-hydroxy-ethyl]-3-isopropyl-ureido}-benzyl)-carbamic acid tert-butyl ester. $^1$H NMR (300 mHz, CDCl$_3$) 8.85 (br s, 1H); 7.45 (m, 2H); 7.3–7.0 (m, 5H); 5.82 (s, 1H); 5.12 (br s, 1H); 4.7 (d, 1H, J=8 Hz); 4.4–4.15 (m, 3H); 3.42 (dd, 1H, J=16 and 8 Hz); 3.1 (d, 1H, J=16 Hz); 1.4 (s, 9H); 1.9 (d, 3H, J=7 Hz); 1.07 (d, 3H, J=7 Hz).

Step 5

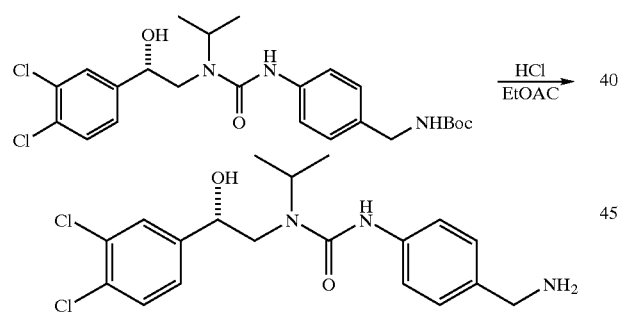

3-(4-Aminomethyl-phenyl)-1-[2-(3,4-dichloro-phenyl)-2-hydroxy-ethyl]-1-isopropyl-urea Through a solution of 3 g (6 mmol) (4-{3-[2-(3,4-Dichloro-phenyl)-2-hydroxy-ethyl]-3-isopropyl-ureido}-benzyl)-carbamic acid tert-butyl ester in 100 mL EtOAc was gently bubbled HCl gas for 15 min. The reaction mixture was then concentrated in vacuo and to the resulting residue was added 15 mL 1N LiOH solution. This was extracted 3×70 ml EtOAc and the combined extracts were washed with 10 ml brine, dried over Na$_2$SO$_4$, filtered and concentrated to give 2.2 g 3-(4-Aminomethyl-phenyl)-1-[2-(3,4-dichloro-phenyl)-2-hydroxy-ethyl]-1-isopropyl-urea as a white solid which was used without further purification. $^1$H NMR(300 mHz, CD$_3$OD) 7.71 (d, 1H, J=2 Hz); 7.53 (d, 1H, J=8 Hz); 7.37 (dd, 1H, J=8 and 2 Hz); 7.28 (m, 4H); 4.88(m, 1H); 4.34 (sept, 1H, J=7 Hz); 3.78 (s, 2H); 3.48(dd, 1H, J=9 and 16 Hz); 3.22 (m, 2H); 1.25 (d, 3H, J=7 Hz); 1.12 (d, 3H, J=7 Hz).

Step 6

1H-Benzoimidazole-5-carboxylic acid 4-{3-[2-(3,4-dichloro-phenyl)-2-hydroxy-ethyl]-3 isopropyl-ureido}-benzylamide To a solution of the amine (0.040 mmol, 17.0 mg) in 0.5 ml DMF was added benzimidazole-4-carboxylic acid (0.044 mmol, 7.1 mg), EDC (0.044 mmol, 8.7 mg), and HOAt (0.044 mmol, 5.9 mg). This solution was stirred for 15 h and purified directly by reverse phase preparatory HPLC (Zorbax 2.5×7 cm C8 column, linear gradient 5–100% CH$_3$CH/H$_2$O$_2$(0.1% TFA), 15 mL/Min). The desired fractions were combined and the solvent removed by vacuum centrifugation to give 1H-Benzoimidazole-5-carboxylic acid 4-{3-[2-(3,4-dichloro-phenyl)-2-hydroxy-ethyl]-3-isopropyl-ureido}-benzylamide (12.6 mg, 60%). $^1$H NMR $\delta_H$ (CD$_3$OD) 9.37 (s, 1H), 8.33 (s, 1H), 8.11–8.10 (d, 1H, J 1.52 Hz), 8.08-8.07 (d, 1H, J 1.53 Hz), 7.88 (s, 1H), 7.63–7.62 (d, 1H, J 1.83 Hz), 7.40-7.28 (m, 5H), 4.57 (s, 2H), 4.36-4.32 (m, 1H), 3.48-3.44 (m, 2H), 2.15 (s, 1H), 1.26-1.23 (d, 3H, J 6.71 Hz), 1.14-1.11 (d, 3H, 6.41 Hz).

EXAMPLE 2

This example illustrates Scheme 2.

Step 1

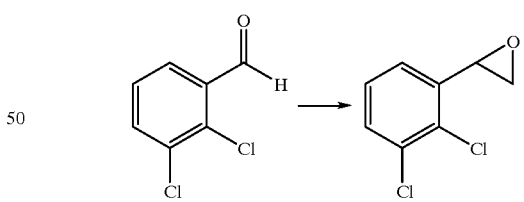

2,3-dichlorophenyloxirane

To a solution of 2,3-dichlorobenzaldehyde (0.314 mmol) in acetonitrile (1 ml) was added solid trimethylsulfonium iodide (0.314 mmol, 64 mg), potassium hydroxide (0.628 mmol, 35 mg), and water (0.079 mmol, 1.4 µl). The heterogeneous mixture were heated in a capped test tube at 60° C. for 3 h. The suspension was then diluted with ethyl acetate (1 ml) and washed with saturated sodium bicarbonate (1×1 ml) and water (3×0.5 ml). The tube was concentrated by vacuum centrifuge over 1 hour and the resulting 2,3-dichlorophenyloxirane used without further purification Step 2

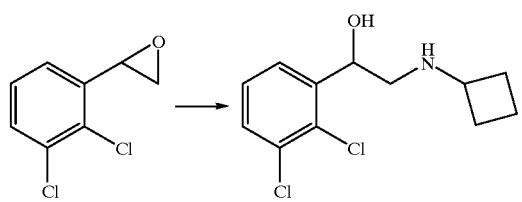

2-cyclobutylamino-1-(2,3-dichlorophenyl)ethanol

To 2,3-dichlorophenyloxirane prepared in step 1 (assumed 0.3 mmol) was added cyclobutylamine (5.86 mmol, 0.5 ml). The solution was heated at 60° C. in a capped test tube overnight. The solution was diluted with water (1 ml), extracted with ethyl acetate (1 ml) and washed with water (2×1 ml). The solution was concentrated by vacuum centrifuge overnight to give 2-cyclobutylamino-1-(2,3-dichlorophenyl)ethanol and used without further purification.

Step 3

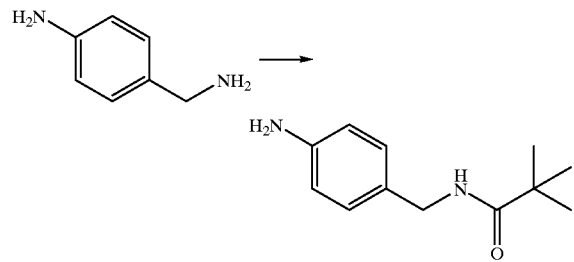

N-(4-amino-benzyl)-2,2-dimethyl-propionamide

To a 0° C. solution of 2.5 ml (22 mmol) 4-aminobenzylamine in 100 mL CH$_2$Cl$_2$ was added 3 mL (22 mmol) triethylamine and 2.7 mL (22 mmol) pivaloyl chloride slowly by syringe over 5 min. and the reaction mixture was warmed to room temperature and stirred 1 hour. Additional portions of. triethylamine (0.4 ml )and pivaloyl chloride (0.4 ml) were added and the reaction mixture was allowed to stir 16 hours. The reaction mixture was then diluted with 400 mL EtOAc, washed with 400 mL each of, saturated aqueous NaHCO$_3$, water, and brine, then dried over Na$_2$SO$_4$, filtered and concentrated. The residue was purified by washing with 100 mL EtOAc, and extracting this wash with 2×100 mL 1N HCl. The combined aqueous extracts were brought to pH>10 with 6M NaOH and extracted 3×100 mL EtOAc. The combined EtOAc extracts were then dried over Na$_2$SO$_4$, filtered and concentrated to give 2.5 g N-(4-amino-benzyl)-2,2-dimethyl-propionamide as a off-white solid. $^1$H NMR (300 mHz, CDCl$_3$) δ 7.15 (d, 2H); 6.65 (d, 2H); 5.75 (b s, 1H); 4.30 (d, 2H); 3.65 (b s, 2H); 1.20 (s, 9H).

Step 4

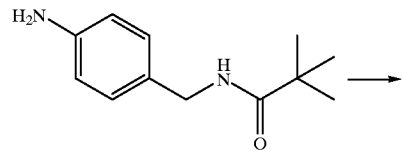

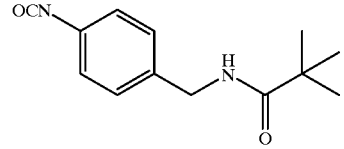

N-(4-isocyanato-benzyl)-2,2-dimethyl-propionamide

To a solution of phosgene (24.1 ml of a 1.93 M solution in toluene, 46.5 mmol) in methylene chloride (50 ml) cooled to 0° C. is added dropwise a solution of N-(4-amino-benzyl)-2,2-dimethyl-propionamide (8 g, 38.8 mmol) and triethyl amine (13.5 ml, 97 mmol) in methylene chloride (80 ml). The reaction mixture is allowed to slowly warm to 25° C. and stirred at this temperature for 18 hrs. The reaction mixture is filtered on dry celite, under an argon atmosphere and the filtrate is concentrated in vacuo. The residue is dissolved in methylene chloride (380 ml) to provide a 0.1 M solution of N-(4-isocyanato-benzyl)-2,2-dimethyl-propionamide in methylene chloride which is used without further purification.

Step 5

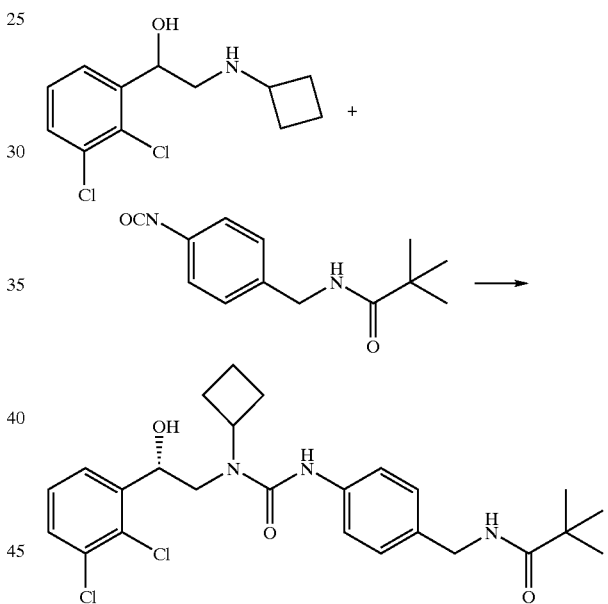

N-(4-{3-[2-(2,3-Dichloro-phenyl)-2-hydroxy-ethyl]-3-cyclobutyl-ureido}-benzyl) -2,2-dimethyl-propionamide To a test tube containing 0.3 mmol 2-cyclobutylamino-1-(2,3-dichlorophenyl)ethanol in 1 ml CH$_2$Cl$_2$ was added 314 μl of a 0.1 M solution of N-(4-isocyanato-benzyl)-2,2-dimethyl-propionamide and 0.43 μl triethylamine. The solution was allowed to stand for 1.5 h, then saturated sodium bicarbonate (1 ml) was added and the resulting mixture extracted with 1 mL EtOAc. The EtOAc extract was washed with water (2×1 ml), and the solvent removed by vacuum centrifugation over 48 h. The resulting solid was dissolved in 450 ml DMF and purified by reverse phase preparatory HPLC (Zorbax 2.5×7 cm C8 column, linear gradient 5–100% CH$_3$CH/H$_2$O (0.1% TFA), 15 mL/Min). The desired fractions were combined and the solvent removed by vacuum centrifugation to give. The desired fractions were combined and placed on a speed vacuum overnight for 15 h to give N-(4-{3-[2-(2,3-Dichloro-phenyl)-2-hydroxy-ethyl]-3-cyclobutyl-ureido}-benzyl)-2,2-dimethyl-propionamide.

¹H NMR δ_H (CD₃OD) 7.67-7.66 (d, 1H, J 1.22 Hz), 7.64-7.63 (d, 1H, J 1.23 Hz), 7.38-7.36 (t, 1H, J 7.94 Hz), 7.28-7.25 (d, 2H, J 8.55 Hz), 7.20–7.17 (d, 2H, J 8.24 Hz), 5.33-5.31 (t, 1H, J5.5 Hz), 4.38-4.31 (m, 4H), 3.59-3.57 (d, 2H, J 5.5 Hz), 2.20-1.99 (m, 4H), 1.68-1.56 (m, 3H), 1.20 (s, 9H).

EXAMPLE 3

This example illustrates Scheme 3.
Step 1

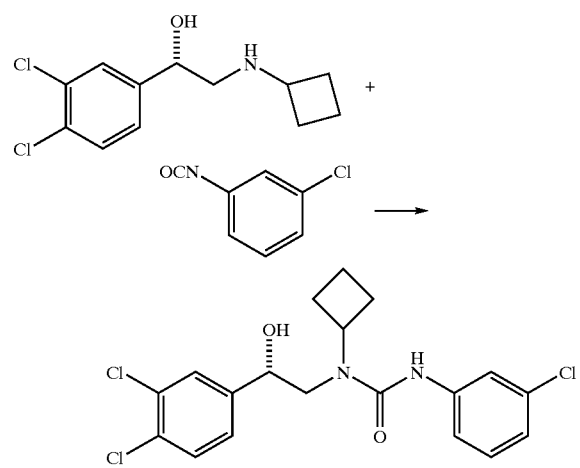

1-Cyclobutyl-1-[2-(3,4-dichloro-phenyl)-2-hydroxy-ethyl]-3-(3-chlorophenyl)-urea To a solution of 0.0116 g (0.076 mmol) of 3-chlorophenyl isocyanate in 200 μL CH₂Cl₂ was added 0.0200 g (0.077 mmol) of amine in 200 μL of CH₂Cl₂. An additional 200 μl of CH₂Cl₂ was added and the solution was mixed by vortex 1 minute. After standing 16 h at room temperature, the reaction mixture was concentrated in vacuo. The resulting material was dissolved in 200 μL DMF and purified by reverse phase preparatory HPLC (Zorbax 2.5×7 cm C8 column, linear gradient 5–100% CH₃CH/H₂O (0.1% TFA), 15 mL/min). The desired fractions were combined and the solvent removed by vacuum centrifugation to give 0.0099 g 1-Cyclobutyl-1-[2-(3,4-dichloro-phenyl)-2-hydroxy-ethyl]-3-(3-chlorophenyl)-urea. ¹H NMR (CDCl₃, 400 MHz) δ 7.530(d, 1H, J=2.10 Hz, ArH); 7.472 (m, 2H, ArH); 7.233 (m, 3H, ArH); 7.028 (m, 1H, ArH); 4.858 (m, 1H, ArCH); 4.242 (m, 1H, NCH(CH₂)₂); 3.600 (dd, 1H, J=8.74 Hz, 15.50 Hz, CH₂); 3.419 (dd, 1H, J=2.28 Hz, 15.45 Hz, CH₂); 2.333 (m, 1H, CH₂); 2.126 (m, 3H, CH₂CH₂); 1.756 (m, 2H, CH₂); MS (Electrospray): m/z 413.05 (M⁺H).

EXAMPLE 4

This example illustrates Scheme 4.
Step 1

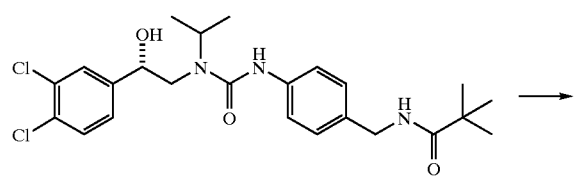

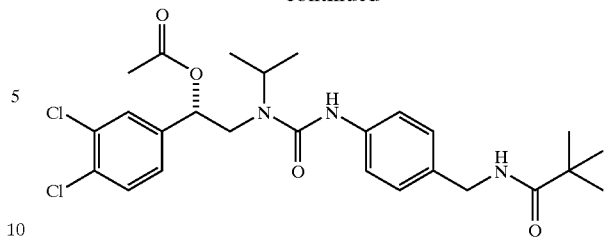

N-(4-{3-[2-(3,4-Dichloro-phenyl)-2-acetoxy-ethyl]-3-isopropyl-ureido}-benzyl)-2,2-dimethyl-propionamide To a solution of 0.02 g (0.41 mmol) N-(4-{3-[2-(3,4-Dichloro-phenyl) -2-hydroxy-ethyl]-3-isopropyl-ureido}-benzyl)-2,2-dimethyl-propionamide in 0.1 mL CH₂Cl₂ was added 0.006 mL triethylamine and 0.029 mL (0.04 mmol from a 1.4M solution in CH₂Cl₂). The reaction mixture was allowed to stand 24 h., then another portion of acid chloride and triethylamine were added. The reaction mixture was allowed to stand 36 more hours, and 0.025 g dimethylaminopyridine was added and the reaction was allowed to stand 24 more hours, then concentrated. The residue was dissolved in 0.2 mL DMF and purified by reverse phase preparatory HPLC (Zorbax 2.5×7 cm C8 column, linear gradient 5–100% CH₃CH/H₂O (0.1% TFA), 15 mL/min). The desired fractions were combined and the solvent removed by vacuum centrifugation to give N-(4-{3-[2-(3,4-Dichloro-phenyl)-2-acetoxy-ethyl]-3-isopropyl-ureido}-benzyl)-2,2-dimethyl-propionamide

EXAMPLE 5

This example illustrates Scheme 5.
Step 1

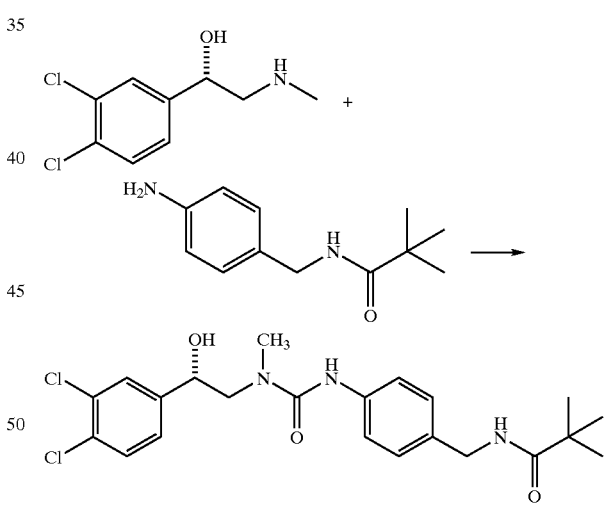

N-(4-{3-[2-(3,4-Dichloro-phenyl)-2-hydroxy-ethyl]-3-methyl-ureido}-benzyl)-2,2dimethyl-propionamide To a 0° C. solution of 0.048 g (0.16 mmol) triphosgene in 1 mL CH₂Cl₂ was slowly added a solution of 0.1 g 0.48 mmol) N-(4-amino-benzyl)-2,2-dimethyl-propionamide and 0.07 mL (0.5 mmol) triethylamine in 8 mL CH₂Cl₂ over 20 min. The reaction mixture was allowed to warm to room temperature for 15 min., then recooled to 0° C. whereupon a solution of 0.2 g (0.9 mmol) 2-methylamino-1-(3,4-dichlorophenyl)ethanol (prepared as in scheme 1, step 2) and 0.1 mL (0.5 mmol) triethylamine in 2 mL CH₂Cl₂ was added. The reaction mixture was allowed to warm to room temperature and stir 1 hour, then diluted with 100 mL EtOAc, washed with 100 mL each of, saturated aqueous NaHCO$_3$, 10% aqueous KHSO$_4$, and brine, then dried over Na$_2$SO$_4$, filtered and concentrated. Purification by flash chromatography (2.5×12 cm silica gel, linear gradient 3–5% MeOH/CH$_2$Cl$_2$) afforded 0.14 g N-(4-{3-[2-(3,4-Dichloro-phenyl)-2-hydroxy-ethyl]-3-methyl-ureido}-benzyl)-2,2-dimethyl-propionamide. $^1$H NMR(300 mHz, CD$_3$OD) δ 7.61 (d, 1H, J=1.83 Hz); 7.49 (d, 1H, J=8.24 Hz); 7.35 (dd, 1H, J=1.83 and 8.24 Hz); 7.26 (d, 2H, J=8.54 Hz); 7.17 (d, 2H, J=8.55 Hz); 4.93 (m, 1H); 4,31 (s, 2H); 3.54 (m, 2H); 2.96 (s, 3H); 1.20 (s, 9H).

EXAMPLE 6

This example illustrates Scheme 6.

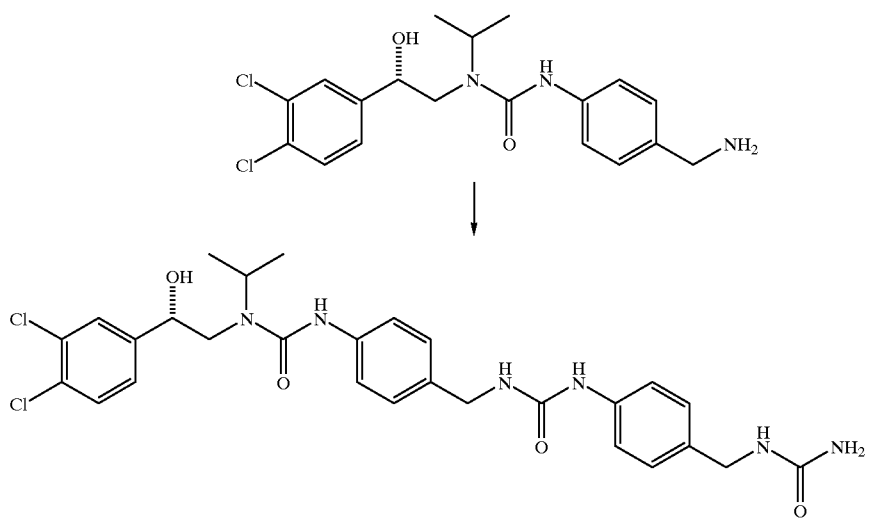

1-[2-(3,4-Dichloro-phenyl)-2-hydroxy-ethyl]-1-isopropyl-3-{4-[3-(4-ureidomethylphenyl)-ureidomethyl]-phen-1-yl}-urea To a solution of 0.11 g (0.33 mmol) triphosgene in 2 ml CH$_2$Cl$_2$ was added a solution of 0.22 g (1 mmol) 4-aminobenzylamine, tertbutylcarbamate and 0.18 ml (1 mmol) diisopropylethylamine in 10 ml CH$_2$Cl$_2$ dropwise over 15 min. After the addition was complete, a solution of 0.4 g (1 mmol) 3-(4-Aminomethylphenyl)-1-[2-(3,4-dichloro-phenyl)-2-hydroxy-ethyl]-1-isopropyl-urea (from Scheme 1, step 5) and 0.18 ml (1 mmol) diisopropylethylamine in 5 ml CH$_2$Cl$_2$ was added over 5 min. The reaction mixture was stirred for 3 h, diluted with 100 ml CH$_2$Cl$_2$, washed with 100 ml each of saturated aqueous NaHCO$_3$, water, and brine, then dried over Na$_2$SO$_4$, filtered and concentrated. Purification by flash chromatography (4×15 cm silica gel, linear gradient 50–100% EtOAc/hexanes) provided 0.45 g that was dissolved in 10 mL EtOAc and cooled to 0° C. A steady stream of HCl gas was passed through the solution for 5 min and after 5 additional minutes the reaction mixture was concentrated in vacuo, suspended in 30 mL EtOAc and treated with 10 mL NaOH (2.5M aqueous solution), then extracted 4×30 mL EtOAc, dried over Na$_2$SO$_4$, filtered and concentrated to give 0.1 g (0.16 mmol) which was dissolved in 8 mL CH$_2$Cl$_2$. To this was added 0.04 mL (0.23 mmol) diisopropylethylamine and the resulting mixture added slowly to a solution of 0.038 g (0.125 mmol) triphosgene in 2 mL CH$_2$Cl$_2$ over 15 min. To the resulting solution was added 5 mL of CH$_2$Cl$_2$ that was saturated with ammonia. After 3 hours the reaction mixture was poured into 300 mL EtOAc, washed 2×200 ml of saturated aqueous NaHCO$_3$, 1×100 mL saturated aqueous ammonium chloride, 1×200 mL water, and 1×200 mL brine, then dried over Na$_2$SO$_4$, filtered and concentrated. The resulting solid was washed with CH$_2$Cl, then purified by reverse-phase preparative HPLC (C18 column, 0–100% linear gradient AcN in H$_2$O containing 0.1% TFA over 40 min). Liopholization afforded 0.01 g. 1-[2-(3,4-Dichloro-phenyl)-2-hydroxy-ethyl]-1-isopropyl-3-{4-[3-(4-ureidomethyl-phenyl)-ureidomethyl]-phen-1-yl}-urea FAB mass spectrum M+H=587.0%). $^1$H NMR δ$_H$ (CD$_3$OD) 7.62 (d, 1H, J=1.8 Hz); 7.52 (d, 1H, J=8.42 Hz); 7.37 (dd, 1H, J=2.02 and 8.24 Hz); 7.33-7.23 (m, 6H); 7.20 (d, 2H, J=8.42 Hz); 4.88 (dd, 1H, J=2.38 and 8.79 Hz); 4.33 (m, 3H); 4.23 (s, 2H); 3.48 (m, 2H); 1.24 (d, 3H, J=6.95 Hz); 1.12 (d, 3H, J=6.59 Hz).

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

EXAMPLE 7

Tablet Preparation

Tablets containing 25.0, 50.0, and 100.0 mg., respectively, of the active drug 1H-Benzoimidazole-5-carboxylic acid 4-{3-[2-(3,4-dichloro-phenyl)-2-hydroxy-ethyl]-3-isopropyl-ureido}-benzamide are prepared as illustrated below:

Table for Doses Containing from 25–100 mg of the Active Compound

| TABLE FOR DOSES CONTAINING FROM 25–100 MG OF THE ACTIVE COMPOUND | | | |
|---|---|---|---|
| | Amount-mg | | |
| Active Drug | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active drug, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 8

Intravenous Formulations

An intravenous dosage form of active drug 1H-Benzoimidazole-5-carboxylic acid 4-{3-[2-(3,4-dichloro-phenyl)-2-hydroxy-ethyl]-3-isopropyl-ureido}-benzylamide is prepared as follows:

| Ingredient | Amount |
|---|---|
| Active Drug | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active drug is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 9

Intravenous Formulation

A pharmaceutical composition was prepared at room temperature using a citrate buffer, and sodium chloride, to obtain a concentration of of 0.25 mg/ml.

800 grams of water was introduced into a standard pharmaceutical mixing vessel. 0.25 grams of active drug 1H-Benzoimidazole-5-carboxylic acid 4-{3-[2-(3,4-dichloro-phenyl)-2-hydroxy-ethyl]-3-isopropyl-ureido}-benzylamide was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| Active drug | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A compound of the formula

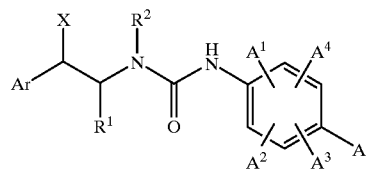

or a pharmaceutically acceptable salt thereof, wherein A is hydrogen or

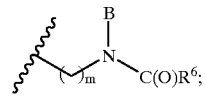

$R^1$ is hydrogen or $C_{1-10}$ alkyl;

Ar is

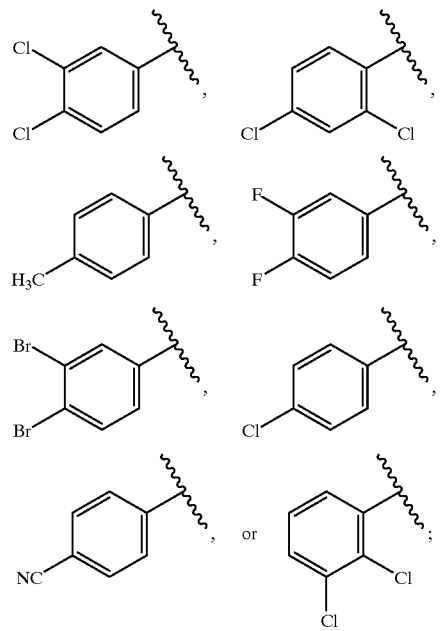

X is
OH,
OCH₃,
OC(O)C(CH₃)₃,
OC(O)CH₃,

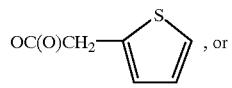, or

OCH₂CH₃;

R² is
CH(CH₃)₂,
C(CH₃)₃, CH₃, CH₂CH₃,

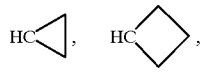

CH₂CH₂CH₃,
CH(CH₃)₂CH₂CH₃,
CH(CH₃)CH₂CH₃, CH(CH₂CH₃)₂, CH(CH₃)CH₂OCH₃,
CH(CH₃)CH₂CH₂CH₃, CH(CH₃)CH₂F, or CH(CH₃)CH₂SCH₃;

A¹ is
hydrogen,
Cl,
F,
CH₃, or
CN;

A² is
hydrogen,
F, or
OCH₃;

A³ and A⁴ are hydrogen;
m is 0, 1, or 2;
B is hydrogen;
R⁶ is
CH(CH₃)₂,
CH₂CH₃,

CH₃,
C(CH₃)₃,
CH₂Ph,
Ph,
C(CH₃)₂NC(O)OC(CH₃)₃,
C(NH₂)(CH₃)₂,

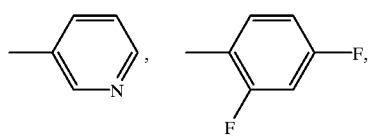

-continued

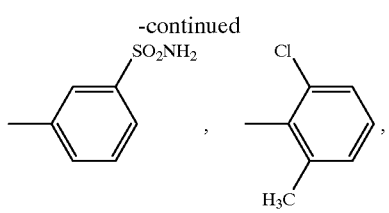

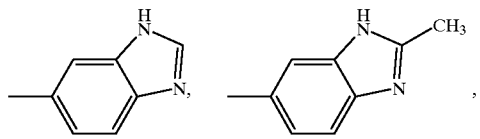

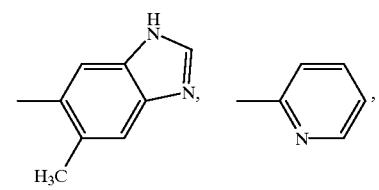

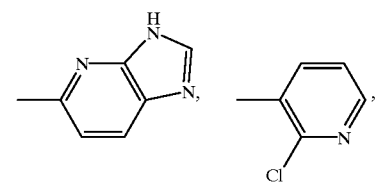

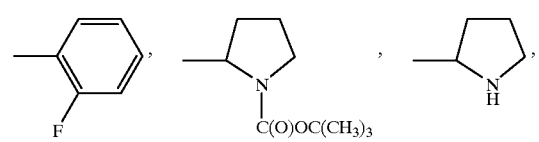

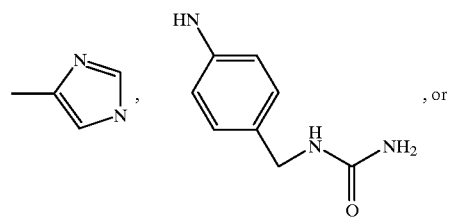

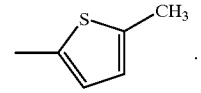

2. A compound of claim 1, or a pharmaceutically acceptable salt thereof, selected from the group consisting of 41 42
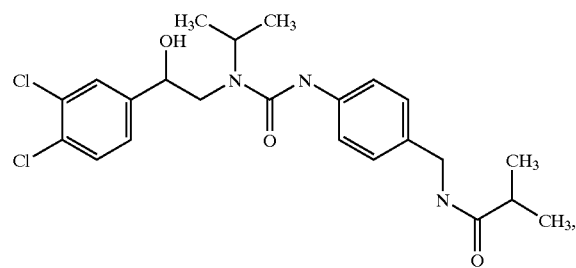
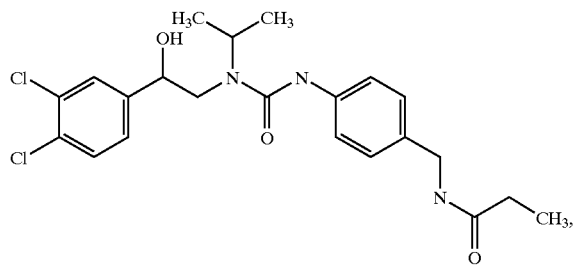
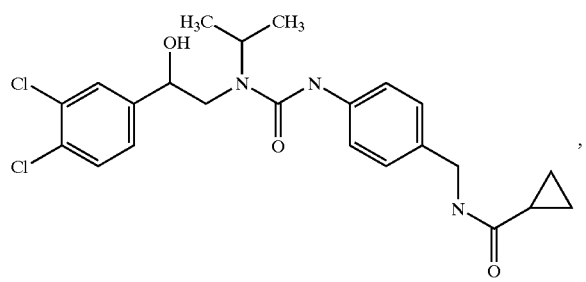
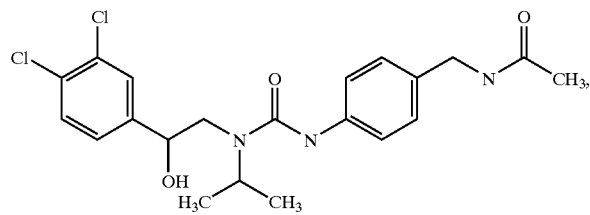
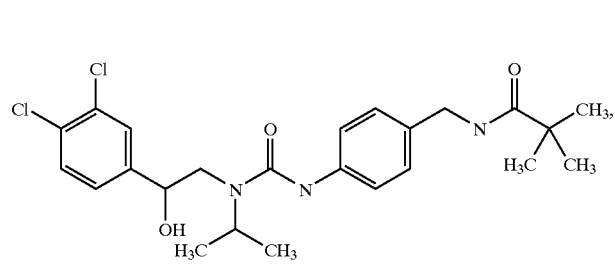
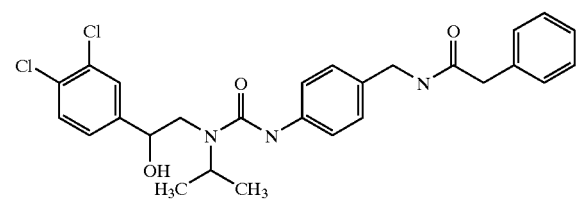
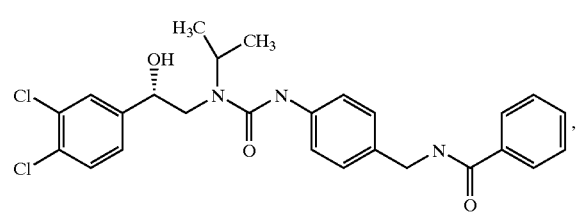
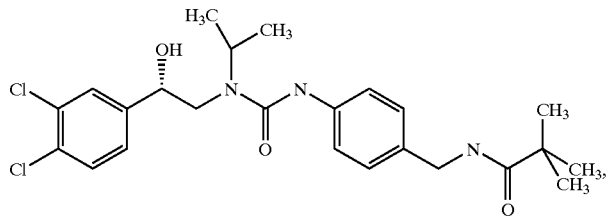
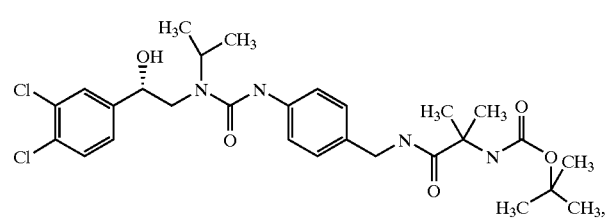
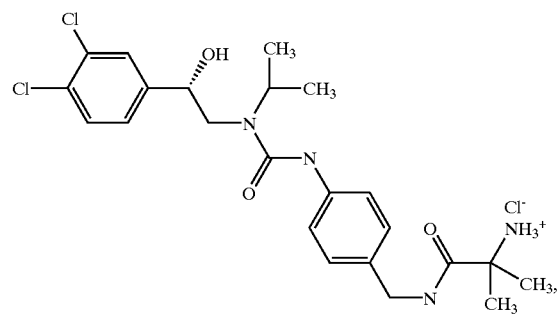
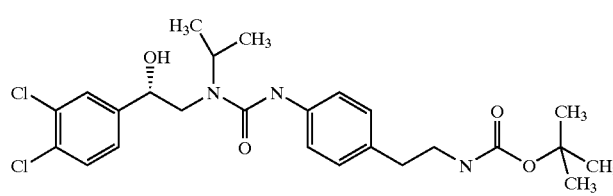
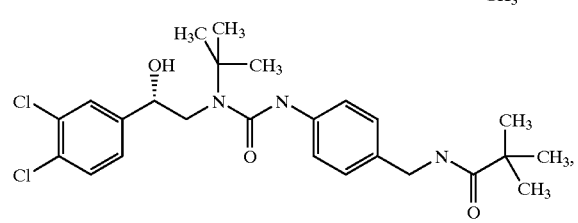

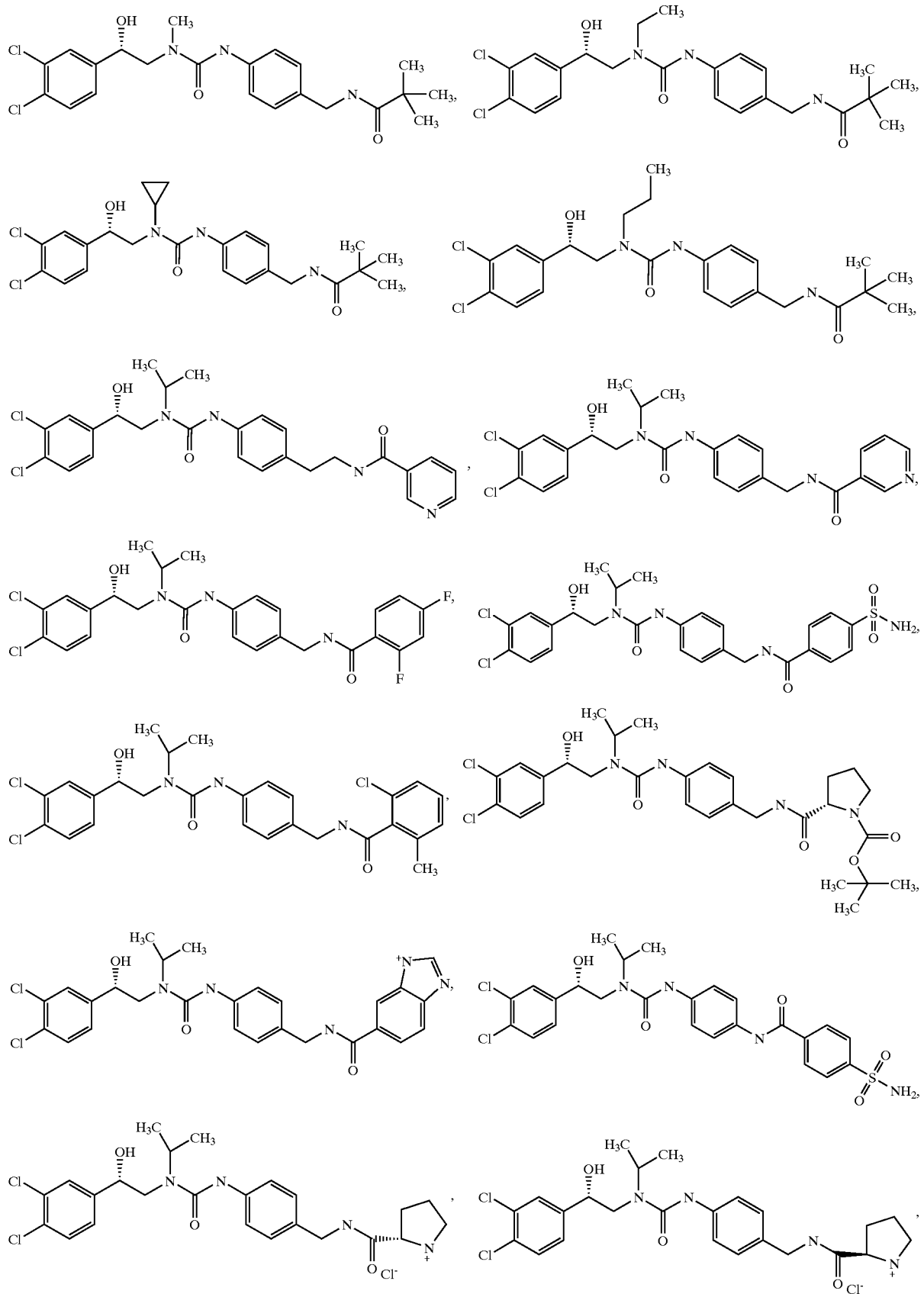

-continued
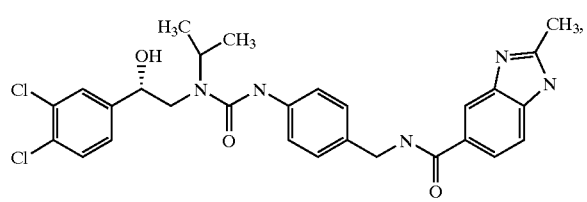
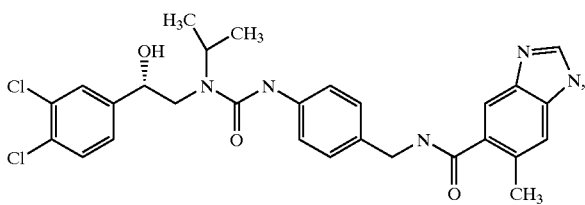
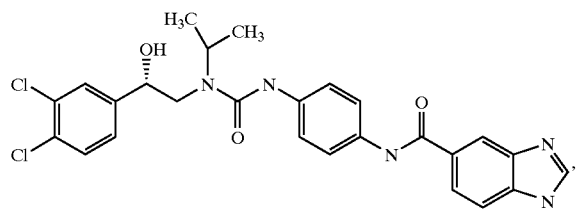
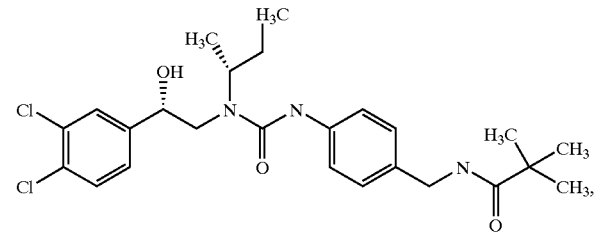
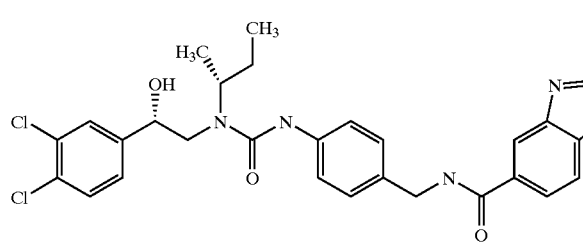
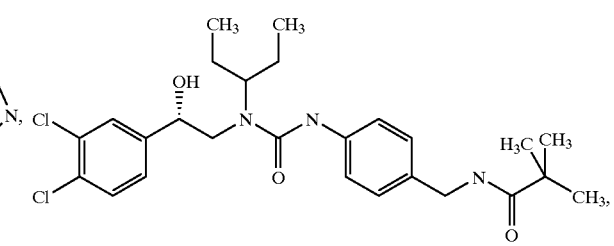
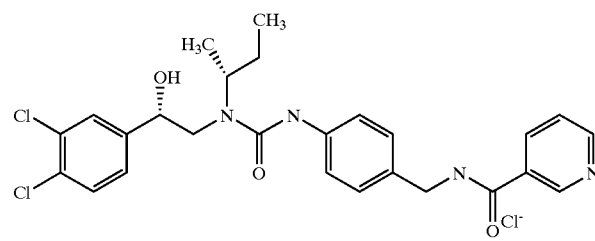
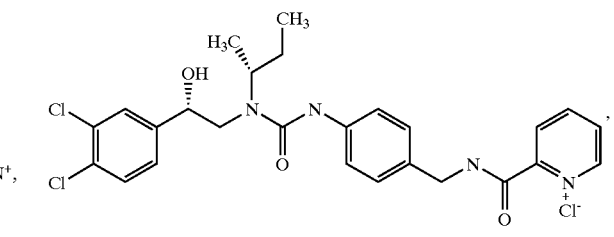
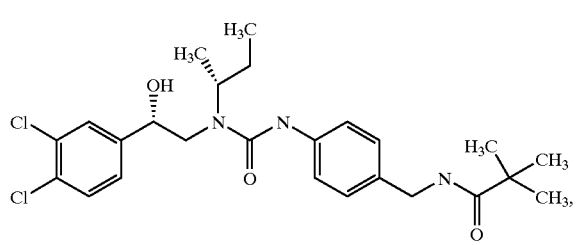
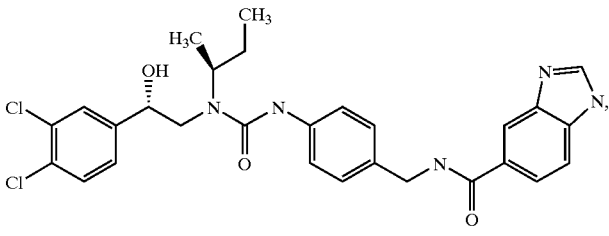
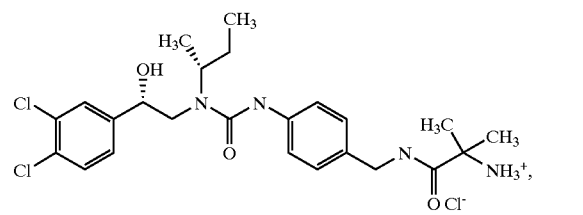
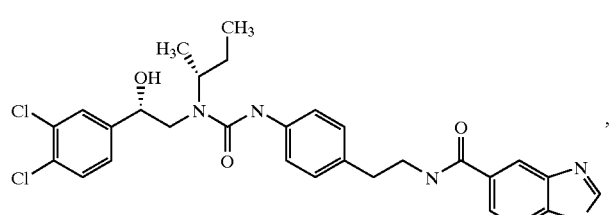
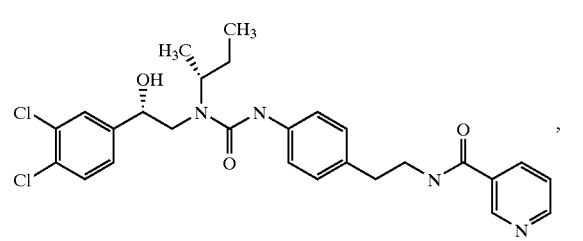
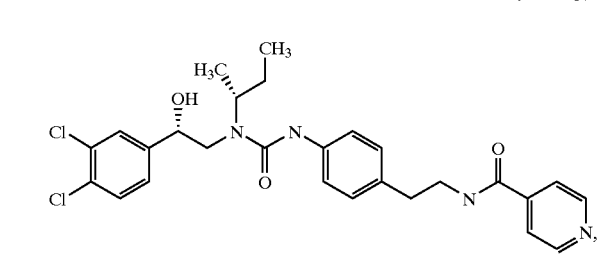

-continued
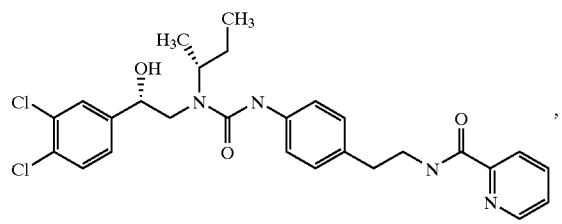
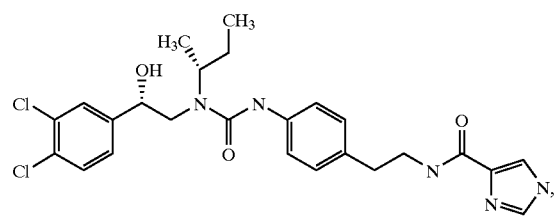
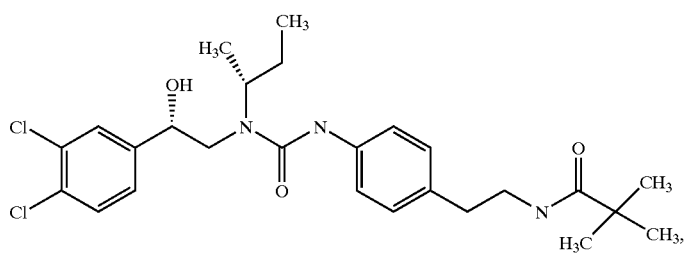
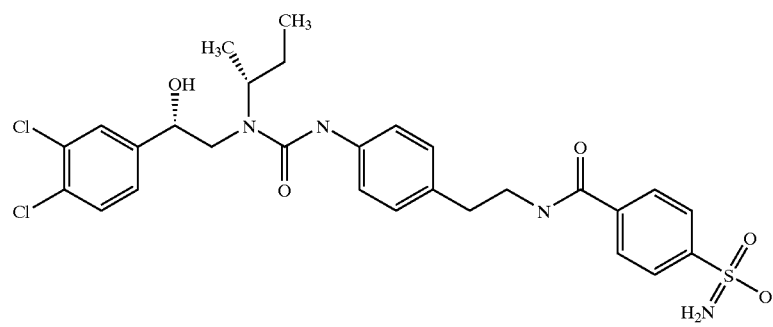
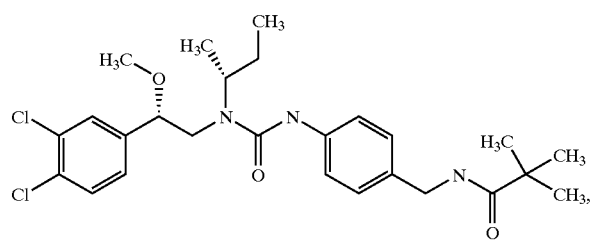
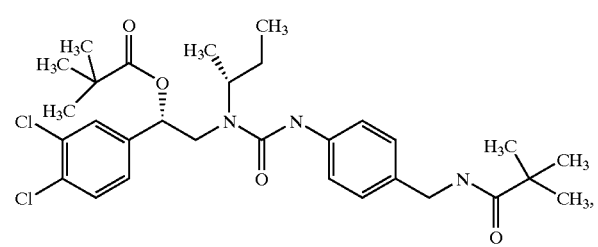
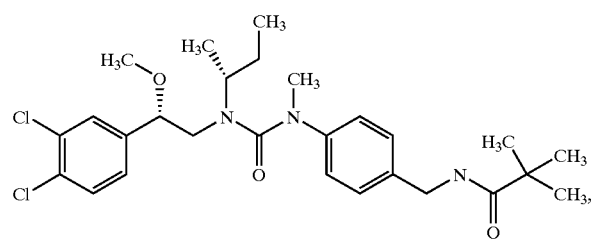
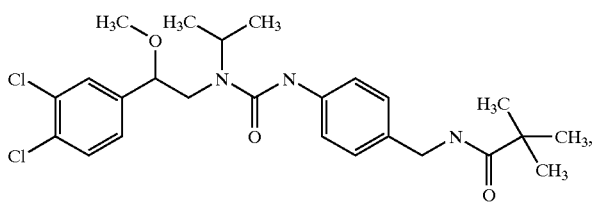
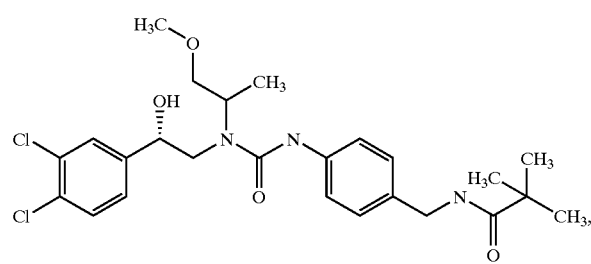
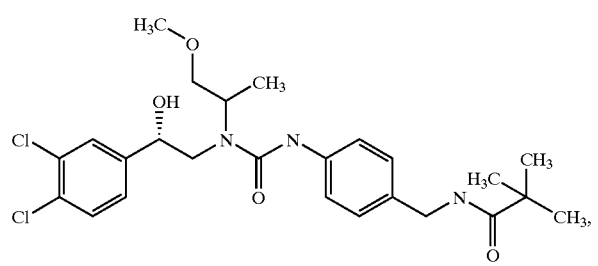

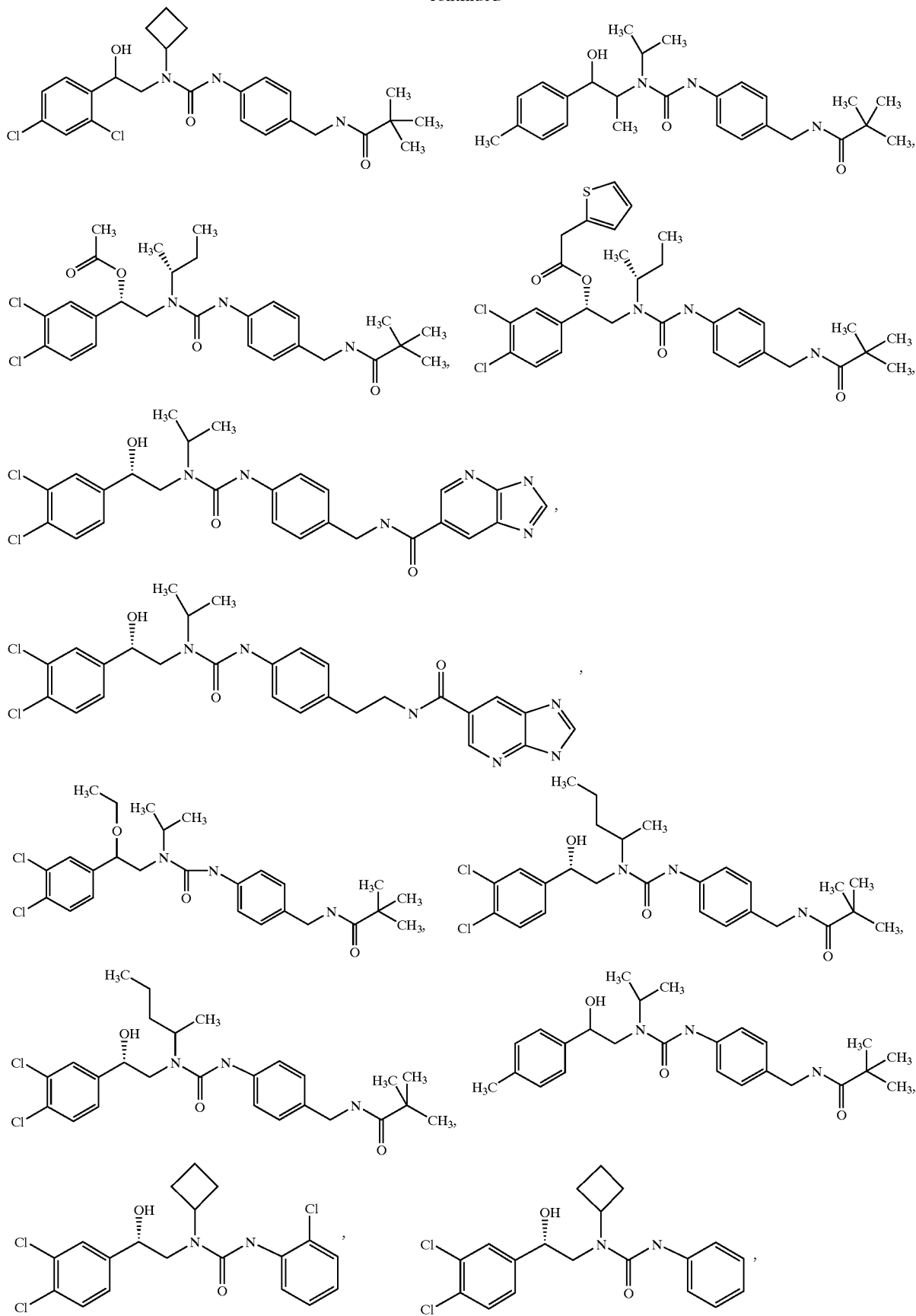

-continued
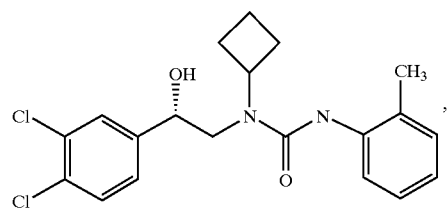
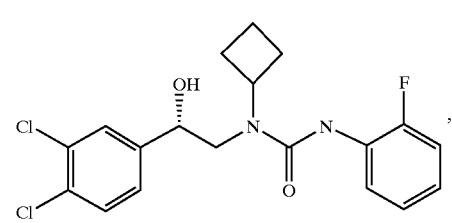
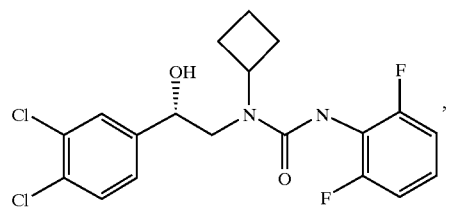
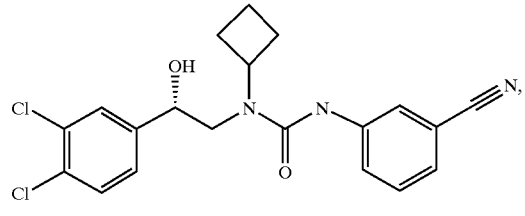
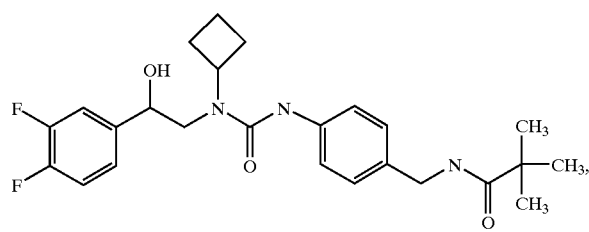
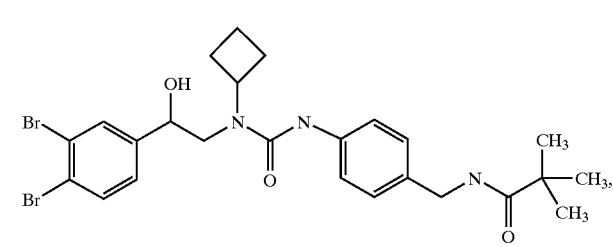
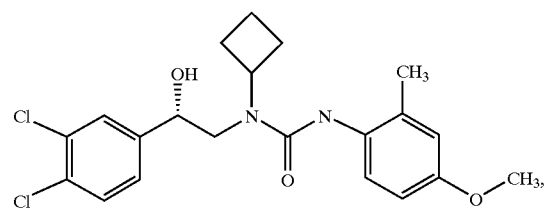
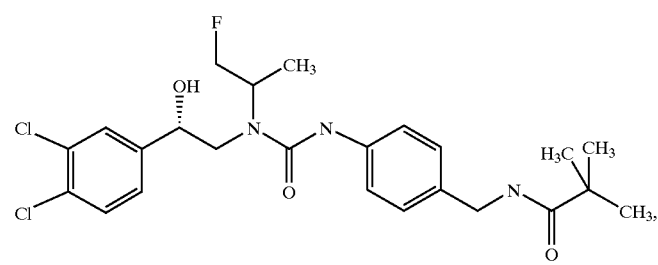
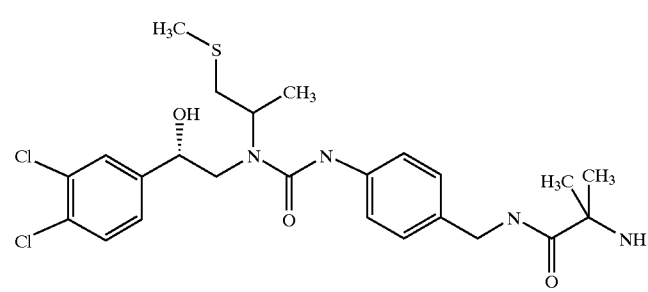
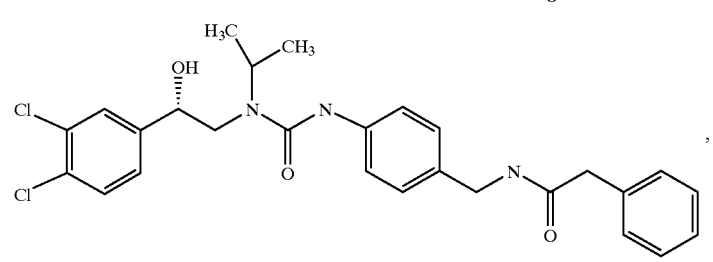

-continued
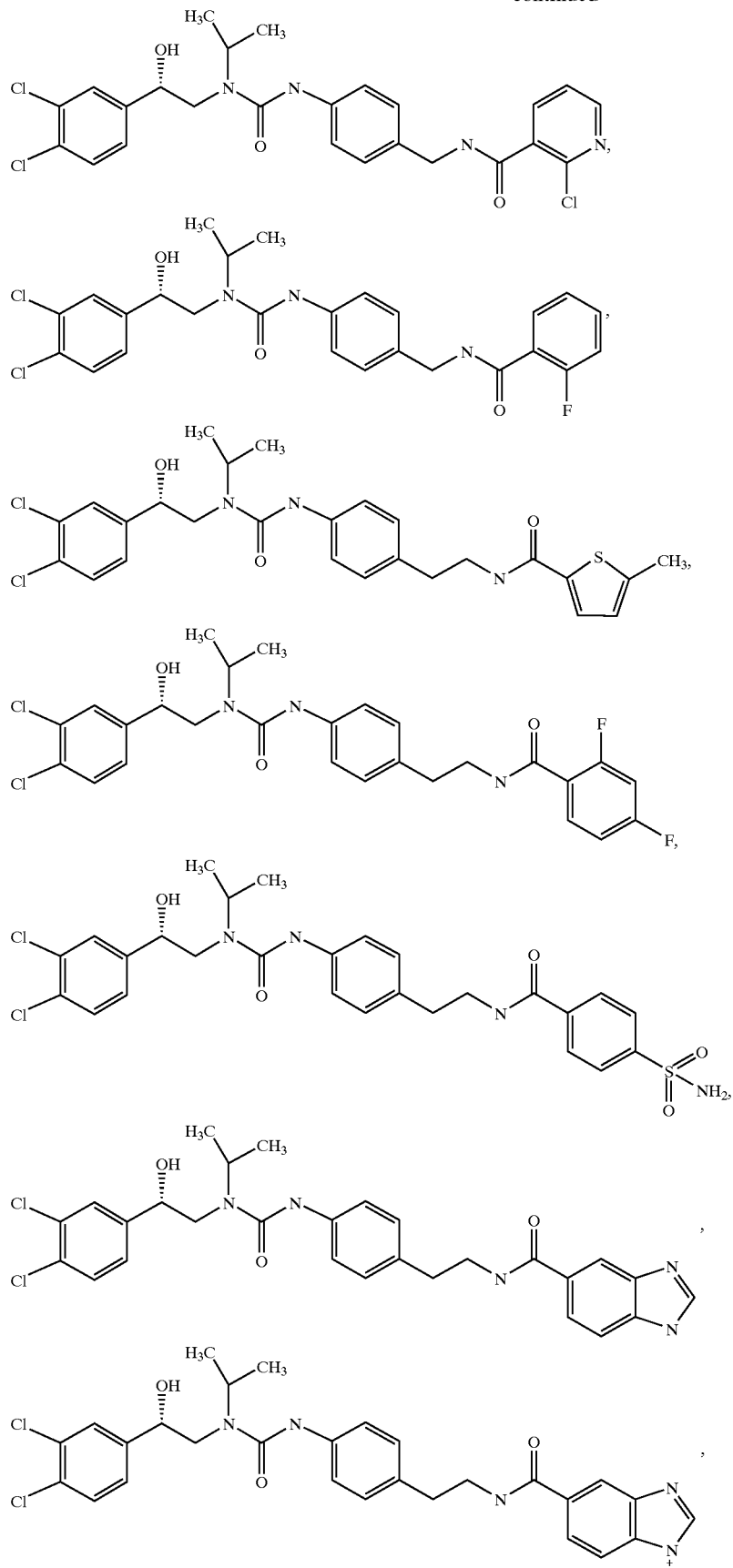

-continued
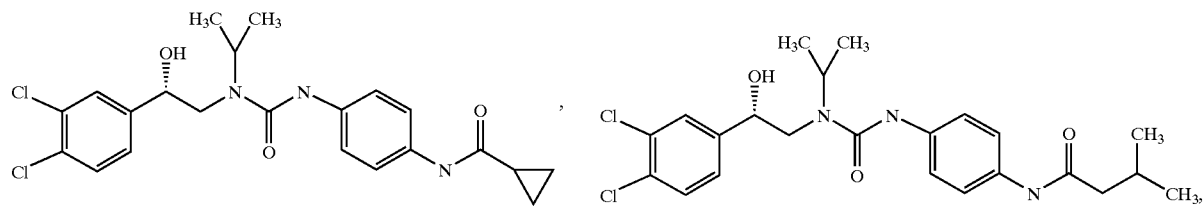
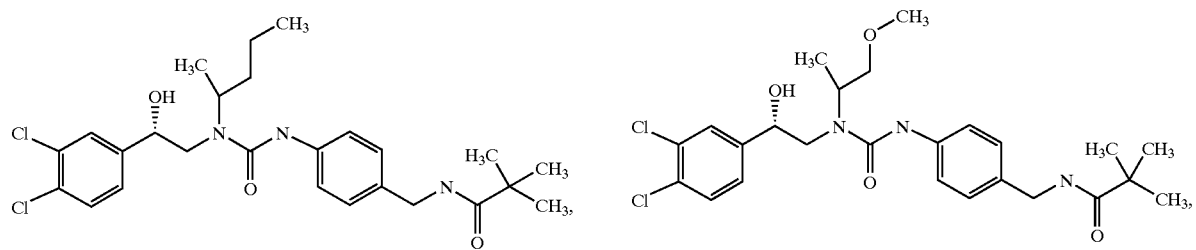
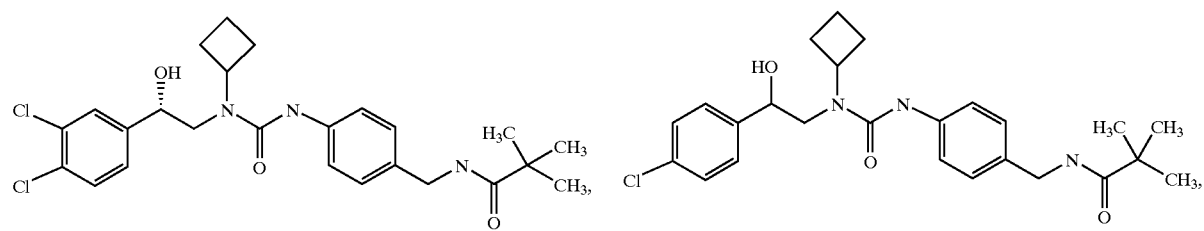
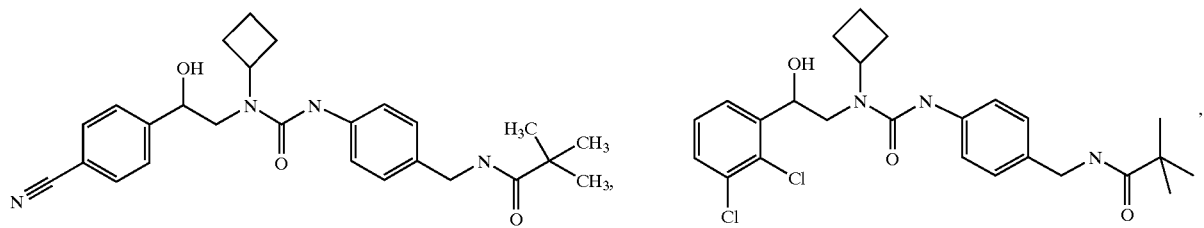
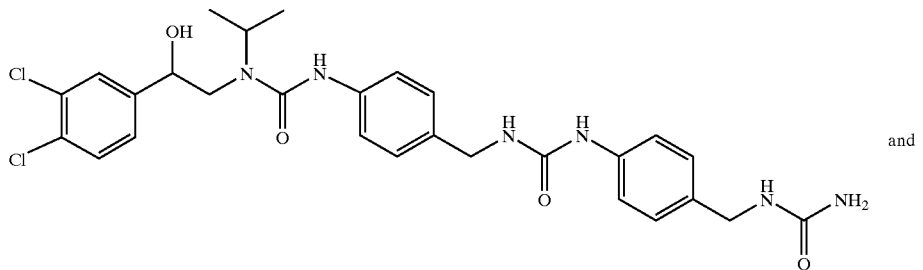
and
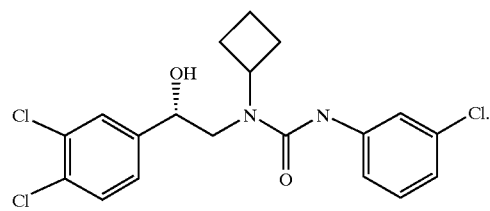

3. A pharmaceutical composition comprising a therapeutically effective amount of a compound of claim 1 and a pharmaceutically acceptable carrier.

4. A method for inhibiting the aggregation of blood platelets in a mammal, comprising treating the mammal with a composition of claim 2.

5. A method for inhibiting the aggregation of blood platelets in a mammal, by blocking thrombin from acting at its receptor site, comprising treating the mammal with a composition of claim 3.

6. A composition for inhibiting the aggregation of blood platelets in a mammal comprising a therapeutically effective amount of a compound of claim 1 in combination with two or more agents selected from a thrombolytic agent, an anticoagulant agent, and an antiplatelet agent and a pharmaceutically acceptable carrier.

7. A composition for inhibiting the aggregation of blood platelets in a mammal comprising a therapeutically effective amount of a compound of claim 1 in combination with a thrombolytic agent and a pharmaceutically acceptable carrier.

8. A composition for inhibiting the aggregation of blood platelets in a mammal comprising a therapeutically effective amount of a compound of claim 1 in combination with an anticoagulant agent and pharmaceutically acceptable carrier.

* * * * *